US009493529B2

(12) United States Patent
Blanche et al.

(10) Patent No.: US 9,493,529 B2
(45) Date of Patent: Nov. 15, 2016

(54) ROBO1-FC FUSION PROTEIN AND USE THEREOF FOR TREATING TUMOURS

(75) Inventors: Francis Blanche, Paris (FR); Beatrice Cameron, Paris (FR); Tarik Dabdoubi, Le Coudray Montceaux (FR); Frederique Dol-Gleizes, Toulouse (FR); Pierre Fons, Toulouse (FR); Catherine Prades, Frouzins (FR); Jean-Pascal Herault, Frouzins (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/641,012

(22) PCT Filed: Apr. 8, 2011

(86) PCT No.: PCT/FR2011/050811
§ 371 (c)(1),
(2), (4) Date: Oct. 12, 2012

(87) PCT Pub. No.: WO2011/128561
PCT Pub. Date: Oct. 20, 2011

(65) Prior Publication Data
US 2013/0039912 A1 Feb. 14, 2013

(30) Foreign Application Priority Data
Apr. 14, 2010 (FR) .................. 10 52829

(51) Int. Cl.
C07K 14/475 (2006.01)

(52) U.S. Cl.
CPC .................. C07K 14/475 (2013.01)

(58) Field of Classification Search
None
See application file for complete search history.

(56) References Cited

U.S. PATENT DOCUMENTS

| | | | |
|---|---|---|---|
| 7,358,351 B2 * | 4/2008 | St. Croix et al. ........... 536/23.1 |
| 2005/0186662 A1 * | 8/2005 | Low ............................... 435/69.4 |
| 2006/0122373 A1 | 6/2006 | McCarthy et al. |
| 2007/0292442 A1 * | 12/2007 | Wan et al. .................. 424/176.1 |
| 2008/0153104 A1 * | 6/2008 | Aburatani et al. ............ 435/7.1 |

FOREIGN PATENT DOCUMENTS

| | | |
|---|---|---|
| TW | 200918558 | 5/2009 |
| WO | WO-97/09351 | 3/1997 |
| WO | WO-99/20764 | 4/1999 |
| WO | WO-99/51625 | 10/1999 |
| WO | WO 99/51625 A3 | 4/2000 |
| WO | WO-03/075860 A2 | 9/2003 |
| WO | WO-2008/065543 A2 | 6/2008 |
| WO | WO 2008/134046 A1 | 11/2008 |
| WO | WO-2008/134046 A1 | 11/2008 |
| WO | WO 2009/032661 A2 | 3/2009 |
| WO | WO 2009/052081 A2 | 4/2009 |
| WO | WO 2009/052081 A3 | 6/2009 |
| WO | WO 2009/052081 A4 | 7/2009 |

OTHER PUBLICATIONS

Liu et al. (Mol. Cell. Neurosci., 26:232-240, 2004).*
Hiller et al. (Nucleic Acids Research, 32: W375-W379, 2004).*
Fawcett et al. (Nature, 360: 481-484, 1992).*
Nural, H.F. et al, The Slit receptor Robo 1 is predominantly expressed via the Dutt1 allternative promoter in pioneer neurons in the embryonic mouse brain and spinal cord, Gene Expression Patterns, vol. 7 No. 8, Oct. 2007, pp. 837-845.
Shen, F. et al, Increased Immunoreactivity to SLIT/ROBO1 in Ovarian Endometriomas, American Journal of Pathology, vol. 175, No. 2, Aug. 2009, pp. 419-488.
Stella, M.C. et al, The Slit/Robo System Suppresses Hepatocyte Growth Factor-dependent Invasion and Morphogenesis, Molecular Biology of the Cell, vol. 20, No. 2, Jan. 2009, pp. 642-657.
Wang, B. et al., Induction of tumor anglogenesis by Slit-Robo signaling and inhibition of cancer growth by blocking Robo activity, Cancer Cell, vol. 4 No. 1, Jul. 2003, pp. 19-29.
Wang, Li-Jing et al, Targeting Slit-Roundabout signaling inhibits tumor angiogenesis in chemical-induced squarnous cell carcinogenesis, Cancer Sci. vol. 99, No. 3, Mar. 2008, pp. 510-517.
Xian, J. et al. Targeted Disruption of the 3p12 Gene, Dutt1/Robo1, Predisposes Mice to Lung Adeno carcinomas and Lymphomas with Methylation of the Gene Promoter, Cancer Research. vol. 64 No. 18, Sep. 2004, pp. 6432-6437.
Angal, S. et al. A Single Amino Acid Substitution Abolishes the Heterogeneity of Chimeric Mouse/Human (IgG4) Antibody, Molecular Immunology, vol. 30, No. 1, 1993, pp. 105-108.
Avci, M.E. et al., Quantification of SLIT-ROBO transcnots in hepatocellular carcinoma reveals two groups of genes with coordinate expression, BMC Cancer, vol. 8, Dec. 2008, p. 392.
Clark, K. et al., Temporal and spatial expression of two isoforms of the Dutt1/Robo1 gene in mouse development, FEBS Letters, vol. 523, Nos. 1-3, Jul. 17, 2002, pp. 12-16.
Database Accession No. Q9Y8N7 dated Mar. 23, 2010.
Hivert, B. et al, Robo1 and Robo2 Are Homophilic Binding Molecules That Promote Axonal Growth, Molecular and Cellular Neuroscience, vol. 21, No. 4, Dec. 2002, pp. 534-545.
International Search Report for PCT/FR2011/050811 dated Jul. 7, 2011.
Jones, C.A. et al, Robo4 stabilizes the vascular network by inhibiting pathologic angiogenesis and endothelial hyperpermeability, Nature Medicine, 2008, pp. 448-453.
Lam, A. et al. Quantification of Expression of Netrins, Slits and Their Receptors in Human Prostate Tumors, International Journal of Cancer, vol. 103, 2003, pp. 306-415.
Liu, Z. et al, Extracellolar Ig domains I and 2 of Robo are important for ligand (Slit) binding, Molecular and Cellular Neuroscience, vol. 26, No. 2, Jun. 2004, pp. 232-240.

(Continued)

*Primary Examiner* — Brad Duffy
*Assistant Examiner* — Nelson B Moseley, II
(74) *Attorney, Agent, or Firm* — Lathrop & Gage LLP; James H. Velema, Esq.

(57) ABSTRACT

The present invention relates to a Robo1-Fc recombinant protein and to the use thereof for treating diseases in which a Slit protein is overexpressed, in particular cancer. The invention also relates to a composition including such a recombinant protein. Another aspect of the invention involves using a Robo1-Fc molecule as a diagnostic tool for detecting the overexpression of a molecule belonging to the Slit family in a patient.

11 Claims, 10 Drawing Sheets

(56) References Cited

OTHER PUBLICATIONS

Morlot, C. et al. Structural insights into the Slit-Robo complex, Proceedings of the National Academy of Sciences, vol. 104, No. 38, Sep. 18, 2007, pp. 14923-14928.

GenBank Database Accession NM_133631, "*Homo sapiens* roundabout, axon guide receptor, homolog 1 (*Drosophila*) (ROBO1), transcript variant 2," 8 pages. (Apr. 8, 2010) (Accessed Feb. 8, 2015 at http://www.ncbi.nlm.nih.gov/nuccore/nm_133631).

GenBank Database Accession BC157861, "*Homo sapiens* roundabout, axon guidance receptor, homolog 1 (*Drosophila*), mRNA (cDNA clone MGC:189756 Image:9057080, complete cds," 4 pages. (May 12, 2008) (Accessed Feb. 8, 2015 at http://www.ncbi.nlm.nih.gov/nuccore/BC157861).

GenBank Database Accession SN: NP_598334, "Roundabout homolog 1 isoform b," 5 pages. Yuasa-Kawada J et al., (Apr. 8, 2010) (Accessed Feb. 8, 2015 at http://www.ncbi.nlm.nih.gov/protein/NP_598334).

GenBank Database Accession SN: AAI12337, "ROBO1 protein," 4 pages. Strausberg RL et al., (Jan. 21, 2006) (Accessed Feb. 8, 2015 at http://www.ncbi.nlm.nih.gov/protein/AAI12337).

Hussain et al. (2006) "A Molecular Mechanism for the Heparan Sulfate Dependence of Slit-Robo Signaling," Journal of Biological Chemistry 281(51): 39693-39698.

Patel et al. (2001) "Slit Proteins are Not Dominant Chemorepellents for Olfactory Tract and Spinal Motor Axons," Development 128:5031-5037.

Whitford et al. (2002) "Regulation of Cortical Dendrite Development by Slit-Robo Interactions," Neuron 33:47-61.

\* cited by examiner

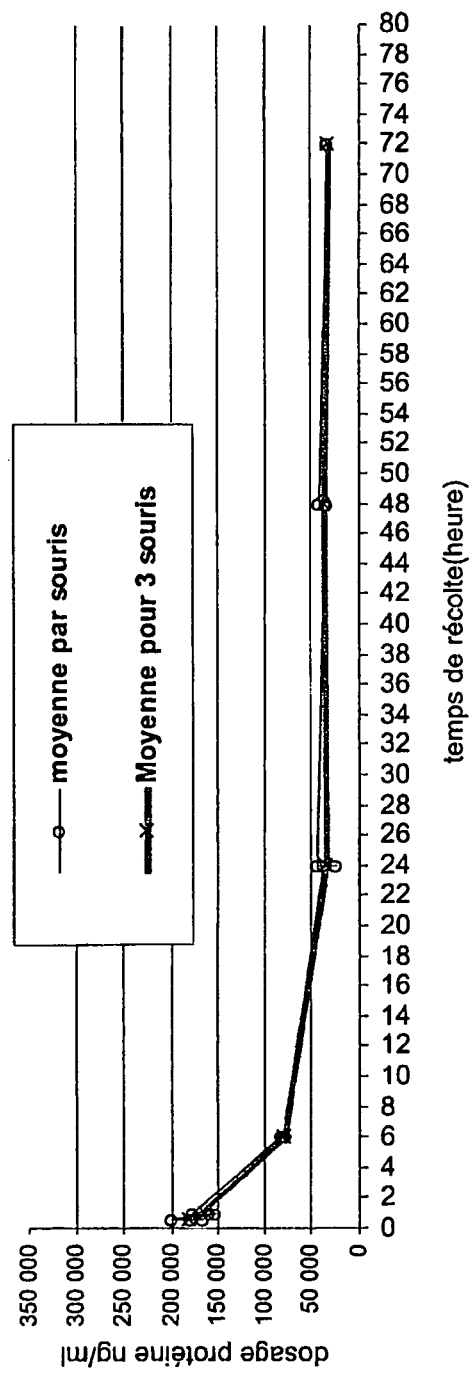
Fig 5-A

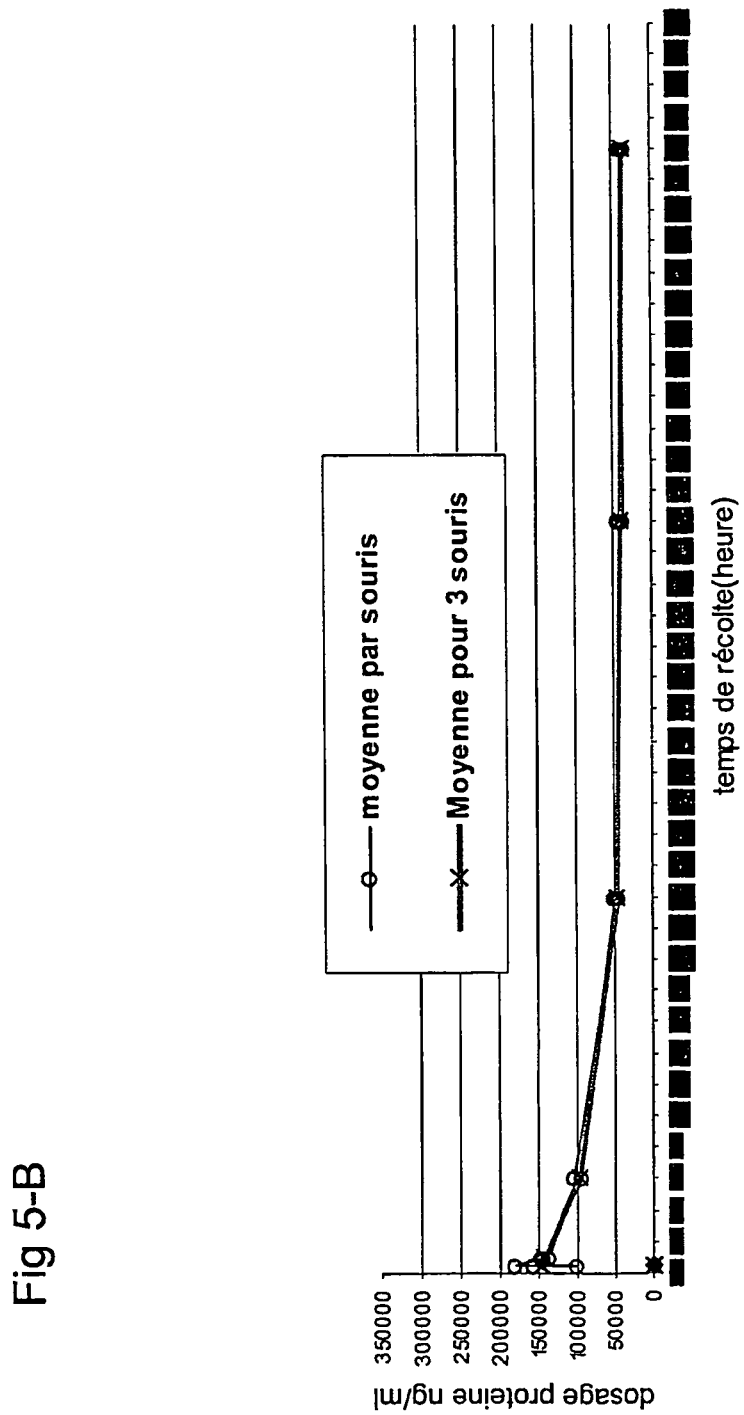
Fig 5-B

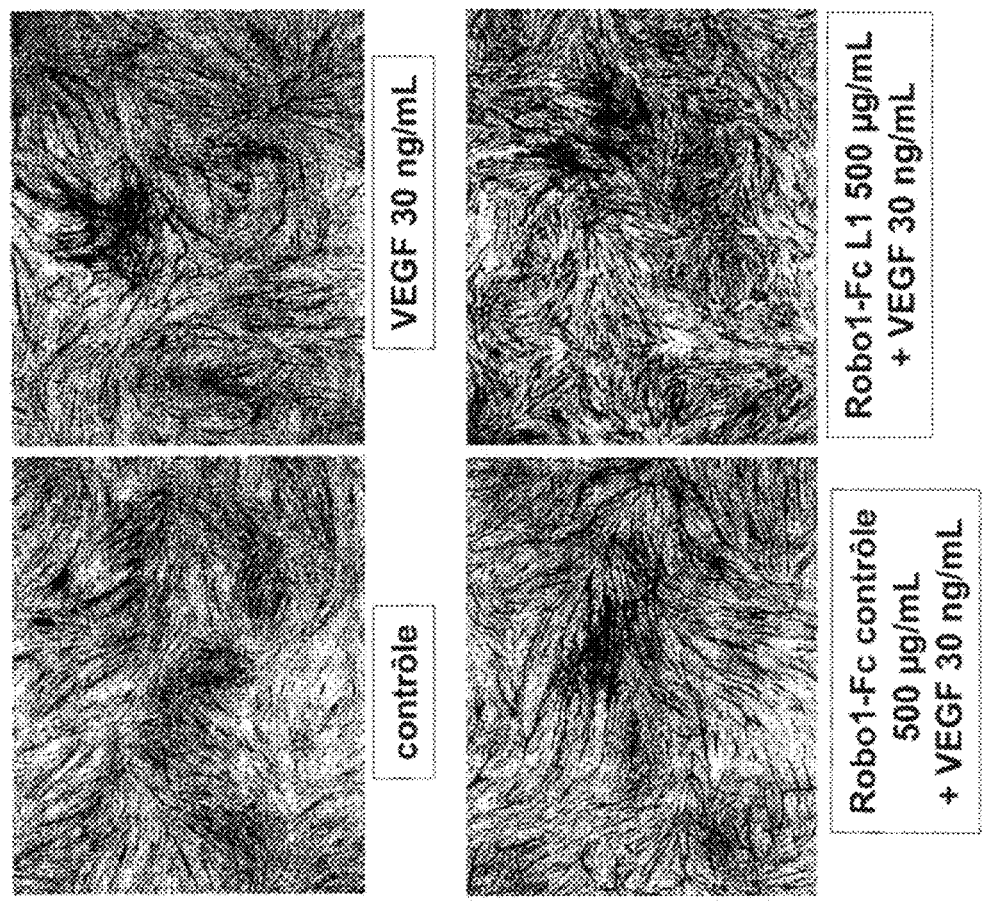
Fig 6-A

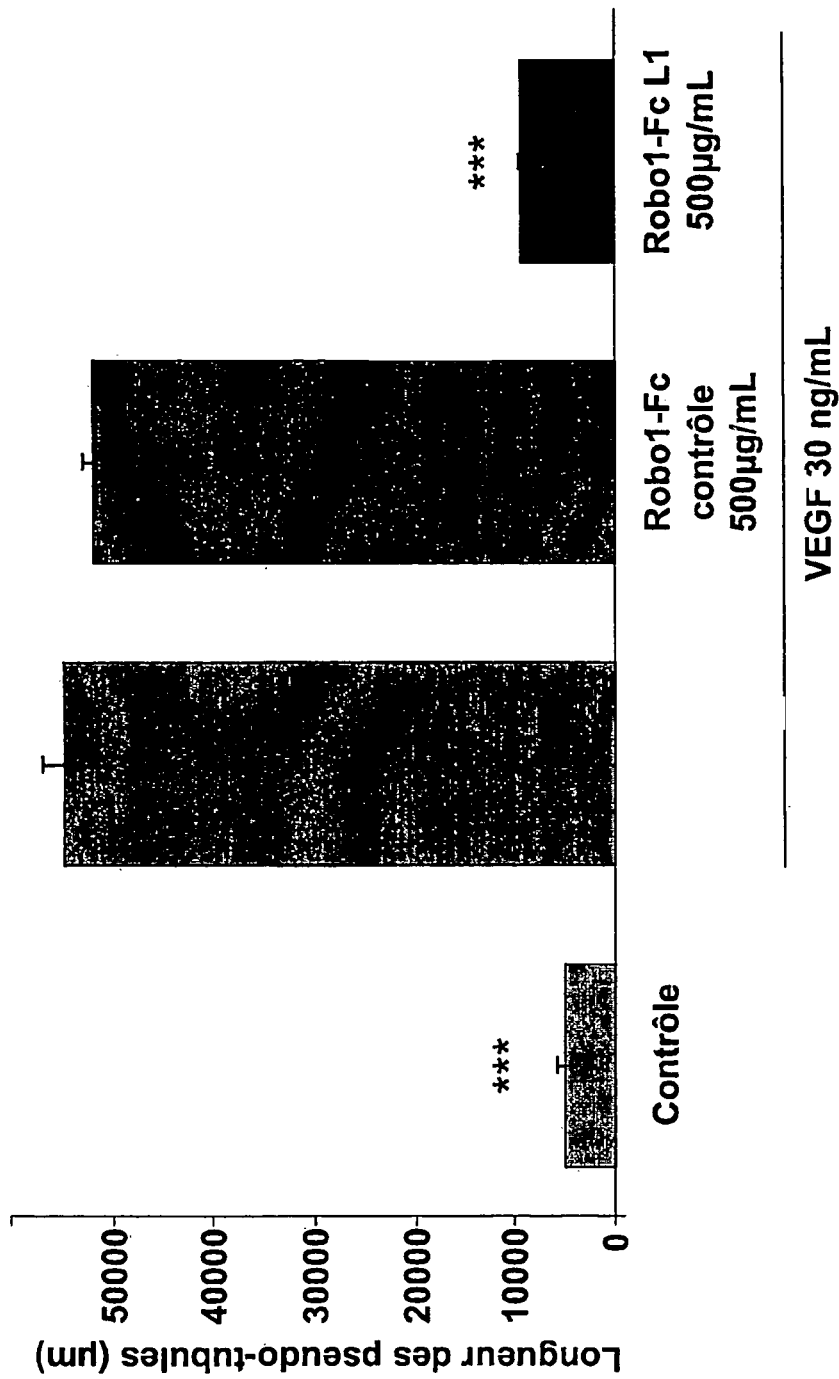
Fig. 6-B

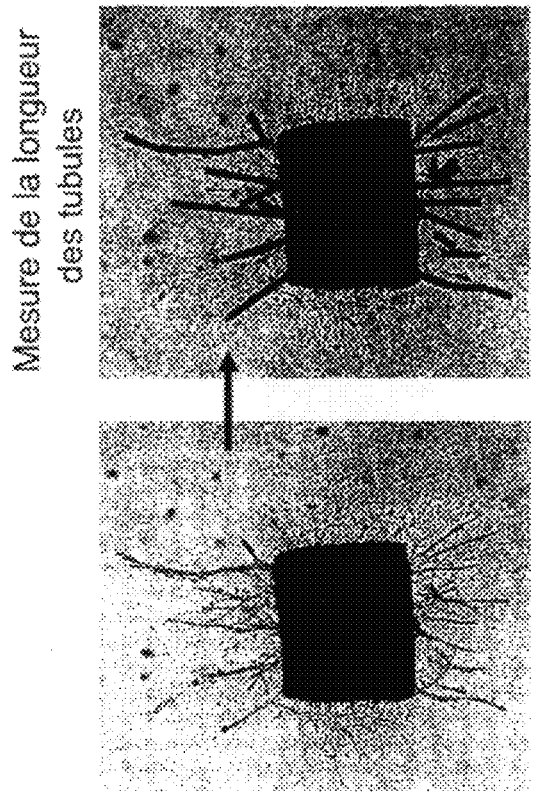
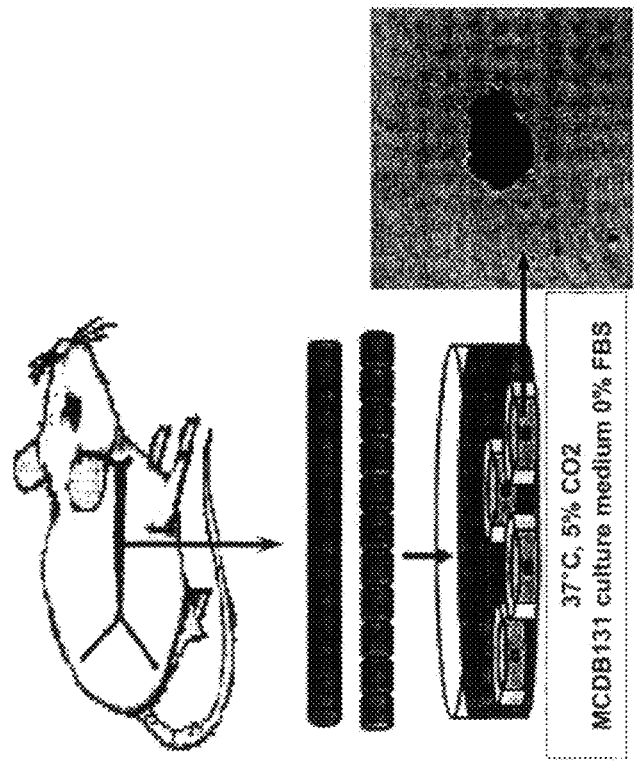
Fig 7-A

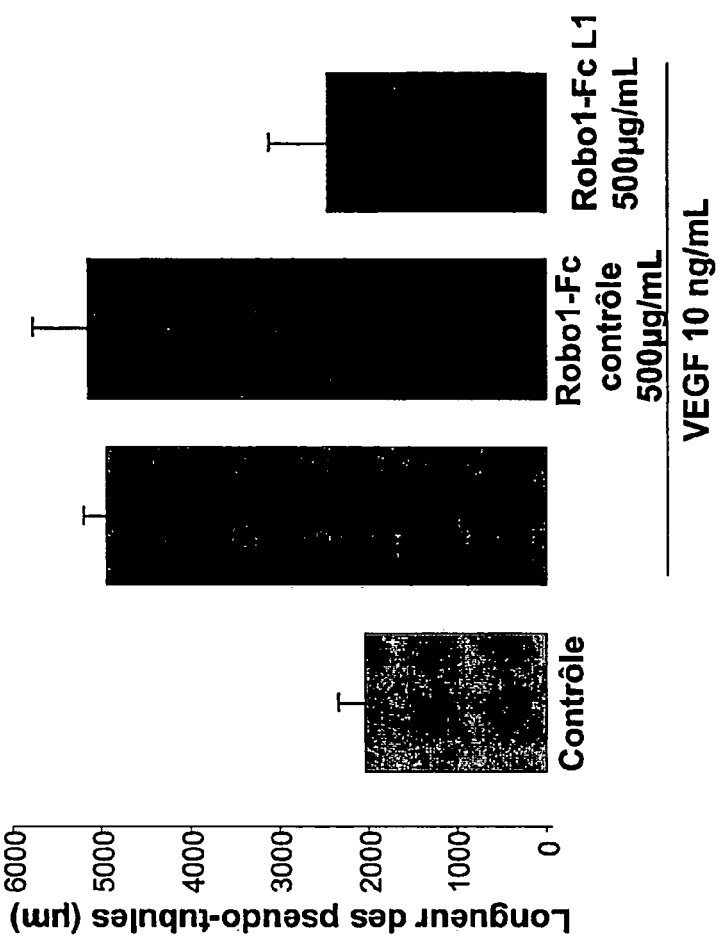
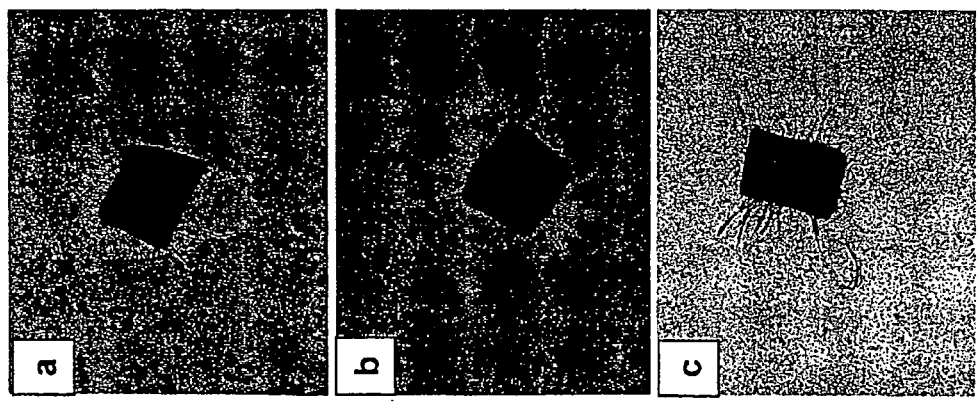
Fig 7-B

ROBO1-FC FUSION PROTEIN AND USE THEREOF FOR TREATING TUMOURS

CROSS-REFERENCE TO RELATED APPLICATIONS

This application is a 371 National Phase Entry application of co-pending International Application PCT/FR2011/050811, filed Apr. 8, 2011, which designated the U.S. and which claims the benefit under 35 U.S.C. §119 of French Application No. 1052829, filed Apr. 14, 2010, both of which are hereby incorporated by reference.

The present invention relates to a recombinant protein Robo1-Fc and to the use thereof for treating diseases in which a Slit protein is overexpressed, in particular cancer. It also relates to a composition comprising such a recombinant protein. Another aspect of the invention consists of the use of a Robo1-Fc molecule as a diagnostic tool for detecting the overexpression of a molecule of the Slit family in a patient.

Slit ligands were first of all described for their role in repelling axonal growth in neuronal development. Since then, the Robo/Slit regulatory pathway has also been described in tumour angiogenesis. Specifically, the Robo4/Slit2 pathway has been described for inhibiting the response of endothelial cells to VEGF (Jones C. A. et al. *Nat. Med* 14, 448-453 (2008)). Regulation by the Robo/Slit pathway makes it possible to channel the excessive proliferation of endothelial non-mature neovessels or buds (non-productive angiogenesis) and to mature these vessels. The expression of Slit2 at the transcriptional level has been demonstrated in several human cancer lines, in particular HCT116 derived from colon carcinoma, Skov-3 derived from ovarian carcinoma. HeLa derived from cervical cancer, MDA-MB-435 derived from melanoma, Hec-1A derived from uterine cancer and, finally, 769-P derived from renal carcinoma (Stella M C et al., Mol Biol Cell. 2009 Vol. 20, Issue 2, 642-657). Overexpression of the Slit2 protein has also been demonstrated on human tissues derived from carcinomas: oral carcinoma (Wang et al. 2008, Cancer Sci. 2008 March; 99(3): 510-7), prostate carcinoma (Latil et al. 2003 Int J Cancer. 2003 Jan. 20; 103(3): 306-15), colon carcinoma (Wang et al. 2003, Cancer Cell, Volume 4, Issue 1, July 2003, Pages 19-29), and liver carcinoma (Avci et al, 2008, BMC cancer, 8: 392). More recently, overexpression of the Slit2 protein has been shown on samples of endometriosis (Shen et al. 2009, *AJP* 175 (2): 479).

The Robo1 protein exists as two isoforms a and b. The extracellar domain of the Robo1 protein isoform b (NP_598334) comprises 5 immunoglobulin domains: Ig1, Ig2, Ig3, Ig4 and Ig5. The Robo protein interacts with the Slit ligands at the level of the Ig1 and Ig2 domains. Liu et al. (2004, Mol. Cell Neurosci. 26: 232-240) have demonstrated the importance of the Ig2 domain in the interaction with Slit and in the activity of Robo (chemorepulsion).

The use of antibodies specific for the Robo1 and the Slit2 proteins has been described in application WO2003/075860. These antibodies make it possible to inhibit tumour angiogenesis.

However, it would be advantageous to propose an alternative approach for treating cancer, in particular a molecule capable of inhibiting the Slit2 signalling pathway.

The inventors have developed a strategy of soluble chimeric Robo1 receptors capable of binding Slit ligands and consequently, of inhibiting the intracellular signalling of the Robo/Slit pathway. Surprisingly, the Robo1-Fc molecules according to the invention have an anti-angiogenesis effect by preventing the formation of mature vessels and not by inhibiting the proliferation of endothelial cells.

DETAILED DESCRIPTION OF THE INVENTION

A subject of the present invention is a Robo-Fc recombinant protein comprising the extracellular domain of the Robo1 protein, isoform b or a part of this domain, a junction region (linker) and an immunoglobulin Fc domain.

In one particular embodiment, the extracellular domain of the Robo1 protein, isoform b consists of the Ig1 and Ig2 domains. These domains correspond to the peptide of SEQ ID NO. 2 encoded by the nucleotide sequence SEQ ID NO. 1, or a sequence having at least 80%, 85%, 90%, 95% or 99% identity with the sequence SEQ ID NO. 2.

The fusion protein also comprises a junction region, also called "linker". In the context of the present invention, the linker makes it possible to give the recombinant protein stability, in particular by limiting in vivo cleavage. Linkers that can be used in a Robo1-Fc molecule are, for example, GluArgProSerPheVal and GlyGlyGlyGlySer. Those skilled in the art have sufficient knowledge to select a linker suitable for this use.

The Fc domain of the Robo1-Fc recombinant molecules according to the invention corresponds to a crystallizable fragment of an immunoglobulin. This Fc fragment can come from various immunoglobulins IgG1 IgG2, IgG3 or IgG4. It is responsible for the effector function of the immune response (WO2008/065543).

In one embodiment according to the invention, the Fc domain comes from an IgG4 immunoglobulin. In one particular embodiment, at least one point mutation or deletion has been introduced into the IgG4 Fc domain so as to increase the stability of the molecule, in particular by stabilizing the hinge region made up of the two Fc domains (Angla et al., 1993, *Mol. Immunol.*, 30: 105-108), to reduce or eliminate the residual activity of the IgG4-Fc, in particular the effector activity (WO 97/09351), and to increase the homogeneity during the production of the recombinant protein. In particular, at least two point mutations, preferably three point mutations, have been introduced into the IgG4 Fc domain. In the Robo1-Fc L1. Robo1-Fc L2 and Robo1-Fc L3 molecules according to the invention, the preferred mutations are the following:

S241P (Kabat numbering) in order to stabilize the disulphide-bridge bonding in the Fc hinge region;

L248E (Kabat numbering) in order to eliminate the residual effector activity of the IgG4-Fc domain;

absence of the C-terminal lysine in order to reduce the heterogeneity of the protein.

Robo1-Fc molecules according to the invention comprising the Ig1 and Ig2 domains of Robo1 isoform b, a linker and a mutated IgG4 domain as described above are Robo1-Fc L1, Robo1-Fc L2 and Robo1-Fc L3.

Robo1-Fc L1 corresponds to the protein of sequence SEQ ID NO. 4, encoded by the nucleotide sequence SEQ ID NO. 3.

Robo1-Fc L2 corresponds to the protein of sequence SEQ ID NO. 6, encoded by the nucleotide sequence SEQ ID NO. 5.

Robo1-Fc L1 and Robo1-Fc L2 differ by virtue of the nature of the linker.

Robo1-Fc L3 corresponds to the protein of sequence SEQ ID NO. 24, encoded by the nucleotide sequence SEQ ID NO. 23.

In one particular embodiment of the invention, one or more point mutations or deletions have been introduced in order to increase the homogeneity during production. In particular, one amino acid, preferably two amino acids, have been truncated in the N-terminal position. Such a Robo-1-Fc molecule according to the invention is the Robo1-Fc L3 molecule, in which the two amino acids (Ser20 and Arg21) have been truncated and in which the amino acid Leu 22 has been fused to the signal peptide of interleukin 2.

The homogeneity of the Robo1-Fc molecules according to the invention is also increased by deleting the C-terminal Lys as previously described.

A subject of the invention is also proteins of which the protein sequence corresponds to the sequences SEQ ID NO. 2, SEQ ID NO. 4, SEQ ID NO. 6 or SEQ ID NO. 24 or has at least 80%. 85%, 90%. 95% or 99% identity with the sequences SEQ ID NO. 2, SEQ ID NO. 4, SEQ ID NO. 6 or SEQ ID NO. 24. These protein variants have the same biological activity as the proteins having the sequence SEQ ID NO. 2, SEQ ID NO. 4, SEQ ID NO. 6 SEQ ID NO. 24, in particular their ability to interact with the proteins of the Slit family.

The Robo1-Fc proteins according to the invention can be produced by transfection of expression plasmids encoding these proteins into any cell type suitable for the expression of eukaryotic recombinant proteins: HEK293, CHO, etc., and then recovered in the culture supernatant and purified according to conventional methods.

Characterization of the Robo1-Fc L1, Robo1-Fc L2 and Robo1-Fc L3 proteins according to the invention has made it possible to confirm that they have the qualities required for their administration as a biotherapeutic agent.

A Robo1-Fc protein according to the invention has the ability to interact with a protein of the Slit family.

The Robo1-Fc proteins according to the invention specifically recognize the human Slit1, Slit2 and Slit3 proteins and the murine Slit2 protein, in particular by interaction with their D2 domain. Their affinity is similar with respect to the 3 members of the Slit family.

Another subject according to the invention corresponds to the nucleic acid molecules encoding the proteins according to the invention.

Thus, the nucleic acid molecules corresponding to the sequences SEQ ID NO. 1, SEQ ID NO. 3, SEQ ID NO. 5 or SEQ ID NO. 23 or having at least 80%, 85%, 90%, 95% or 99% identity with the molecules having the sequence SEQ ID NO. 1, SEQ ID NO. 3, SEQ ID NO. 5 or SEQ ID NO. 23 are part of the invention.

Another subject according to the invention consists of the use of a Robo1-Fc protein according to the invention for treating diseases in which a protein of the Slit family is overexpressed.

The proteins of the Slit family which can be targeted by the Robo1-Fcs according to the invention are Slit1, Slit2 or Slit3.

It has been shown that Robo1 can interact with the various members of the Slit family. Consequently, it is advantageous to note that the Robo1-Fc proteins according to the invention are capable of simultaneously inhibiting the signalling pathways mediated by Slit1, Slit2 and Slit3, which makes it possible to broaden the therapeutic spectrum in comparison with the antibodies which are specific for only one of these pathways.

In another embodiment, a Robo1-Fc protein is used for treating diseases in which a protein of the Slit family is overexpressed, by inhibiting angiogenesis without inhibiting endothelial cell proliferation. This anti-angiogenic activity linked to a vessel maturation defect is called "non-productive angiogenesis".

Specifically, the experimental studies have shown that the Robo1-Fc molecules according to the invention are capable of inhibiting the formation of tubules, without inhibiting endothelial cell proliferation. They make it possible to very significantly reduce the tumour volume in a murine model of lung cancer.

In one preferred embodiment, the Robo1-Fc proteins that can be used for treating diseases in which a Slit protein is overexpressed are Robo1-Fc L1, Robo1-Fc L2 and Robo1-Fc L3, and the molecules which are derived therefrom, include, in particular, point mutations or deletions aimed at increasing the homogeneity during production without significantly modifying the biological properties of these molecules.

In general, the diseases that can be treated with a Robo-1-Fc protein according to the invention are all the diseases in which inhibition of the Slit pathway can have a therapeutic effect, in particular the diseases in which a protein of the Slit family is overexpressed, and in particular those in which Slit2 is overexpressed.

Since the Robo1-Fc molecules according to the invention specifically bind the Slit2 molecule, it is interesting to note that said molecules are capable of simultaneously inhibiting the two pathways in which Slit2 is involved, namely the Robo1/Slit2 and Robo4/Slit2 pathways.

The Robo1-Fc proteins according to the invention can therefore be used for treating cancer, in particular pancreatic cancer, colon cancer, colorectal cancer with or without lymphatic metastasis, breast cancer, lung cancer and lung metastases, ovarian cancer, cervical cancer, melanomas, renal cancer, oral cancer, prostate cancer, liver cancer, etc.

In one particular embodiment, the Robo-Fc proteins are used for treating lung cancer and lung metastases.

The Robo1-Fc molecules according to the invention can also be used as an anticancer medicament as an alternative to or as a supplement to the current therapies.

In particular, these molecules can be administered in combination (optionally simultaneously) with anticancer compounds.

Another subject of the invention relates to a composition comprising a Robo1-Fc protein as defined above and one or more pharmaceutically acceptable excipients.

The Robo1-Fc proteins according to the invention can be formulated in pharmaceutical compositions with a view to topical, oral, parenteral, intranasal, intravenous, intramuscular, subcutaneous, intraocular, etc., administration. Preferably, the pharmaceutical compositions contain pharmaceutically acceptable vehicles for an injectable formulation. They may in particular be isotonic sterile saline solutions (monosodium or disodium phosphate, sodium, potassium, calcium or magnesium chloride, etc., or mixtures of such salts), or dry, in particular freeze-dried, compositions which, by addition, as appropriate, of sterilized water or of physiological saline, allow the formation of injectable solutes.

Another aspect of the invention consists of the use of a Robo1-Fc molecule as a diagnostic tool for detecting the overexpression of a molecule of the Slit family in a patient. This is because it has been shown that the Slit pathway is implicated in many cancers. The provision of a test for evaluating a disturbance of the Slit signalling pathway is very useful for the purpose of selecting patients capable of responding to a treatment based on the administration of a Robo1-Fc molecule.

This diagnostic tool may be in the form of a ready-to-use kit, comprising a Robo1-Fc molecule in a form suitable for it to be brought into contact with a biological sample from a patient (blood, urine, tumour biopsy) liable to exhibit an overexpression of a Slit molecule. The Robo-Fc molecule can optionally be prelabelled, and the combination of Robo-Fc and Slit is detected so as to evaluate an increase in the expression of a Slit protein in the biological sample in comparison with a control sample. This kit can, for example, be in the form of an ELISA kit.

DESCRIPTION OF THE FIGURES

FIG. 5: Pharmacokinetic profile of the Robo1-Fc proteins after an iv injection in mice. A. Administration of Robo1-Fc L1, B. Administration of Robo1-Fc L2.

FIG. 6: Effect of the Robo1-Fc L1 molecule in a coculture test with endothelial cells and mesenchymal cells. A. Robo1-Fc L1 inhibits tubule formation in culture. B. Robo1-Fc L1 significantly inhibits VEGF-induced pseudotubule formation.

FIG. 7: Evaluation of the effect of the Robo1-Fc L1 molecule on an ex vivo aortic ring model in mice. A: Description of the protocol for preparing an aortic ring and for measuring tubules. B: a. Control; b. Robo1-Fc Slit2-minus 500 µg/mL+VEGF 10 ng/mL; Robo1-Fc L1 500 µg/mL+VEGF 10 ng/mL.

EXAMPLES

Example 1

Preparation of the Robo1-Fc Proteins a. Constructs allowing the expression of the Robo1-Fc recombinant proteins used as biotherapeutic agents.

The Robo1-Fc recombinant proteins consist of a fusion between the first two immunoglobulin domains (Ig1-Ig2) of the human Robo1 protein, isoform b (NP_598334) and the Fc domain of human immunoglobulin G4 (hIgG4-Fc, SwissProt IGHG4_HUMAN).

Figure 1:
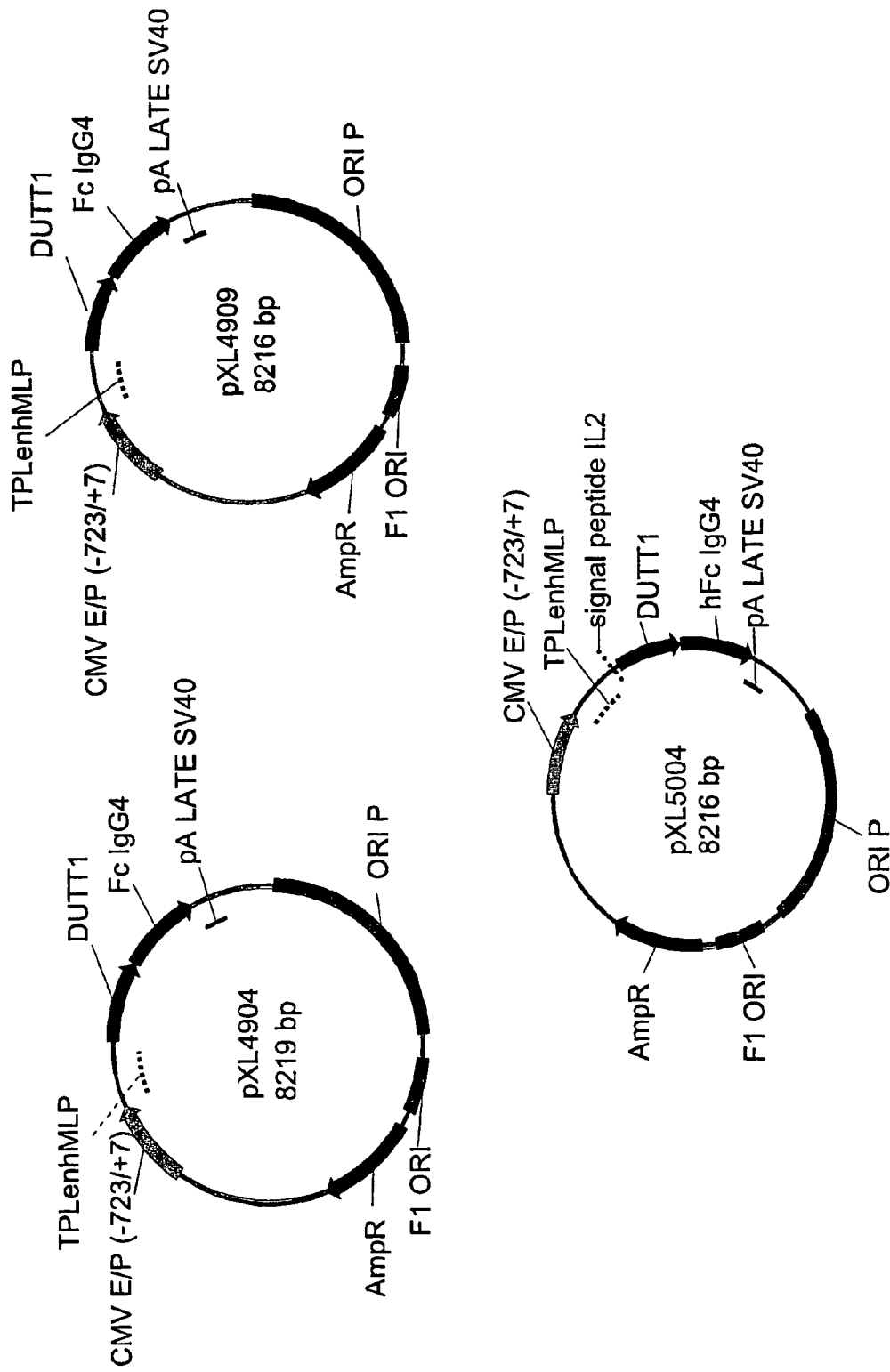
FIG. 1: Expression plasmids for the Robo1-Fc L1 Robo1-Fc L2 and Robo1-Fc L3 proteins.

In order to obtain the Robo1-Fc L1 construct, a fragment of the cDNA (SEQ ID NO. 1) corresponding to the immunoglobulin (Ig) domains Ig1 and Ig2 of this protein (SEQ ID NO. 2) followed by a GluArgProSerPheVal linker was amplified by PCR using the human foetal heart cDNA library (ref. HL5042T, Clontech). This amplified fragment was then cloned into the eukaryotic expression vector pXL4904 (described in FIG. 1) such that the two Ig domains of Robo1 are expressed as a fusion with the Fc domain of human IgG4 in the C-terminal position. Three point mutations were introduced into the IgG4-Fc domain in order to obtain the following characteristics: S241P (Kabat numbering) in order to stabilize the disulphide-bridge bonding in the Fc hinge region; L248E in order to eliminate the residual effector activity of the IgG4-Fc domain; absence of the C-terminal lysine in order to reduce the heterogeneity of the protein. The cDNA sequence used to express this recombinant protein corresponds to the sequence SEQ ID NO. 3. The recombinant protein obtained is called Robo1-Fc L1 and corresponds to the protein sequence SEQ ID NO. 4.

In order to obtain the Robo1-Fc L2 construct, the same cDNA corresponding to the Ig1-Ig2 domains but without the linker mentioned was cloned into the eukaryotic expression vector pXL4909 (described in FIG. 1), which allows the expression of these Ig domains as a fusion with the same Fc domain of IgG4 containing the 3 point mutations described in the construction of Robo1-Fc L1, but this time introducing a GlyGlyGlyGlySer linker upstream of the Fc domain. The cDNA sequence used to express this recombinant protein corresponds to the sequence SEQ ID NO. 5. The recombinant protein obtained is called Robo1-Fc L2 and corresponds to the protein sequence SEQ ID NO. 6.

b. Construction of the Robo1-Fc proteins used as controls

In order to obtain the Robo1-Fc Slit2-minus construct, the cDNA previously cloned into the pXL4904 plasmid was modified by PCR so as to introduce the point mutations allowing the substitutions of the leucine at position 38 to glutamine and the phenylalanine at position 89 to tyrosine. The cDNA sequence used to express this recombinant protein corresponds to the sequence SEQ ID NO. 7. The recombinant protein obtained is called Robo1-Fc Slit2-minus and corresponds to the protein sequence SEQ ID NO. 8.

In order to obtain the Robo1-Fc heparin-minus construct, the cDNA cloned into the pXL4904 plasmid was modified by PCR so as to introduce the point mutations allowing the substitutions of the arginine at position 97 to aniline and the lysine at position 98 to alanine. The cDNA sequence used to express this recombinant protein corresponds to the sequence SEQ ID NO. 9. The recombinant protein obtained is called Robo1-Fc heparin-minus and corresponds to the protein sequence SEQ ID NO. 10.

c. Production of the various Robo1-Fc proteins

The two proteins Robo1-Fc L1 and Robo1-Fc L2 were produced by transient transfection in the HEK293 line (FreeStyle 293-F cells ref 51-0029. Invitrogen, according to the supplier's recommendations) using the pXL4904 and pXL4909 plasmids, respectively, and the helper plasmids pXL4544 and pXL4551 allowing the expression of two N-glycan glycosylation enzymes, i.e. α-2,3-sialyltransferase and β-1,4-galactosyltransferase, as has been described in application WO2008/065543. These proteins were also produced by transfection in the CHO line (CHO-S cells, ref 11619-012. Invitrogen, according to the supplier's recommendations) using the pXL4904 and pXL4909 plasmids, respectively.

The Robo1-Fc L1 and Robo1-Fc L2 proteins expressed in the culture natant of the HEK293 cells were purified by chromatography on a protein A affinity column (MabSelect ref. 17-5199-02, Amersham Biosciences) and elution in 20 ml, NaCl/100 mM acetic acid buffer, and then formulated in PBS buffer (ref. 14190-094, Invitrogen).

The Robo1-Fc Slit2-minus and Robo1-Fc heparin-minus recombinant proteins were produced and purified in the same way.

d. Physicochemical characterization of the Robo1-Fc recombinant proteins

SDS-PAGE and gel permeation analysis made it possible to show that the proteins were dimeric and more than 96% pure. Mass spectrometry analysis made it possible to demonstrate the identity of these proteins, the measured weight of the deglycosylated protein being in perfect agreement with the weight calculated in silico. Analysis of the monosaccharide composition and quantification of the N-glycan sialic acids as described by Saddic et al. 2002. (Methods Mol. Biol. 194: 23-36 and Anumula et al. 1998. Glycobiology 8: 685-694) made it possible to demonstrate that the proteins were sialylated to a very great extent. The results are given in table 1. It will be noted that the N-terminal analysis of the Robo1-Fc L1 and Robo1-Fc L2 molecules showed that these purified proteins contained a variable proportion (0 to 40%) of a form with the first 2 residues (Ser20 and Arg21) truncated.

TABLE 1

Robo1-Fc protein identity

|  | Robo1-Fc L1 | Robo1-Fc L2 |
| --- | --- | --- |
| Weight (SDS-PAGE reducing conditions) | 56 kDa | 55 kDa |
| Weight (SEC, HPLC) | 180 kDa | 180 kDa |
| Weight (LC/MS after deglycosylation) | 48812 Da | 48410 Da |
| N-Glycan profile (HPLC) | highly sialylated 21.4% asialoglycans | highly sialylated 20.1% asialoglycans |
| Monosaccharide composition (HPLC) | complex N-glycans entirely fucosylated no O-glycans | complex N-glycans entirely fucosylated no O-glycans |

Example 2

Preparation of the Slit Proteins Used as Ligand

The cDNA encoding the human Slit2 protein corresponds to the reference protein NP_004778. Fragments of this cDNA were amplified by FOR using the human brain cDNA library (ref, 639300, Clontech).

The cDNA corresponding to the D2 domain was cloned into the eurkaryotic expression vector pXL4911 in order to express this domain containing a His tag in the C-terminal position. The cDNA sequence used to express this recombinant protein corresponds to the sequence SEQ ID NO. 11. The recombinant protein obtained is called Slit2-D2 and corresponds to the protein sequence SEQ ID NO. 12.

The cDNA corresponding to the D1-D2 domains was cloned into the eukaryotic expression vector pXL4912 in order to express these two domains containing a His tag in the C-terminal position. The cDNA sequence used to express this recombinant protein corresponds to the sequence SEQ ID NO. 13, The recombinant protein obtained is called Slit2-D1 D2 and corresponds to the protein sequence SEQ ID NO. 14.

The cDNA corresponding to the extracellular part (Nt) of the Slit2 protein was cloned into the eukaryotic expression vector pXL5033 in order to express this protein with a His tag in the C-terminal position. The cDNA sequence used to express this recombinant protein corresponds to the sequence SEQ ID NO. 15. The recombinant protein obtained is called Slit2-N and corresponds to the protein sequence SEQ ID NO. 16.

The cDNA encoding the D2 domain of the murine Slit2 protein, and corresponding to the D2 domain of the described reference protein NP_848919, was obtained from the cDNA cloned into the pXL4911 plasmid. Four fragments making it possible to generate the five point mutations were generated by PCR with pXL4911 as template, and then these fragments were used as template to amplify the cDNA encoding the complete D2 domain by sequential FOR. The protein carries the Thr311Ser, Lys313Arg, Ile329Leu, Ile411Val and Pro418Ala mutations allowing it to be identical to the D2 domain of the murine Slit2 protein. This plasmid makes it possible to express the D2 domain of the murine Slit2 protein with a His tag in the C-terminal position. The cDNA sequence used to express this recombinant protein corresponds to the sequence SEQ ID NO. 17. The recombinant protein obtained is called mSlit2-D2 and corresponds to the protein sequence SEQ ID NO. 18.

The cDNA encoding the human Slit3 protein corresponds to the described reference protein NP_003052. A fragment of this cDNA was amplified by PCR using the human brain cDNA library (ref. 639300, Clontech). The cDNA corresponding to the D2 domain was cloned into the eukaryotic expression vector pXL5020 in order to express this domain containing a His tag in the C-terminal position. The cDNA sequence used to express this recombinant protein corresponds to the sequence SEQ ID NO. 19. The recombinant protein obtained is called Slit1-D2 and corresponds to the protein sequence SEQ ID NO. 20.

The cDNA encoding the human Slit3 protein corresponds to the described reference protein NP_003053. A fragment of this cDNA was amplified by PCR using the human brain cDNA library (ref, 639300, Clontech). The cDNA corresponding to the D2 domain was cloned into the eukaryotic expression vector pXL5021 in order to express this domain containing a His tag in the C-terminal position. The cDNA sequence used to express this recombinant protein corresponds to the sequence SEQ ID NO. 21. The recombinant protein obtained is called Slit3-D2 and corresponds to the protein sequence SEQ ID NO. 22.

The three proteins called Slit2-D2. Slit2-D1D2 and Slit2-N were produced by transient transfection in the HEK293 line (FreeStyle 293-F cells according to the supplier's recommendations, Invitrogen) using the pXL4911 plasmid (respectively, pXL4912 pXL5033).

The Slit2-D2 and Slit2-D1D2 proteins expressed in the culture supernatant of the HEK293 cells were purified by chromatography on an Ni-chelating sepharose column (ref. 17-0409-03, Amersham Biosciences) and elution in imidazole buffer and then formulated in PBS buffer (ref. 14190-094, Invitrogen) adjusted to 1M NaCl. Mass spectrometry analysis (LC/MS) made it possible to demonstrate the identity of these proteins.

The three proteins called mSlit2-D2. Slit1-D2 and Slit3-D2 were produced, purified and characterized in a comparable manner.

Example 3

Study of the Affinity of the Robo1-Fc Recombinant Proteins for the Slit Proteins and for Heparin by Means of Three Methods: ELISA, SPR and FACS a. Affinity of the Robo1-Fc proteins for heparin In order to determine the affinity of the Robo1-Fc constructs for heparin, 2 mg of Robo1-Fc protein, purified and formulated in 10 mM phosphate, pH 7.0, were chromatographed on a heparin column (1 mL HiTrap Heparin-Sepharose HP, GE Healthcare) by elution with a linear gradient of NaCl of from 0 to 1.5 M.

Table 2 indicates the NaCl concentration of 448 mM necessary for eluting the Robo1-Fc L1 protein as described in the literature (Fukuhara, N. et al. 2008 J. Biol. Chem. 283 p 16226-16234).

TABLE 2

Affinity of Robo1-Fc for heparin

| Robo1-Fc construct | Detachment from the heparin column [NaCl], mM |
|---|---|
| Robo1-Fc L1 | 448 |
| Robo1-Fc Heparin-minus | No binding |

These results show that the Robo1-Fc heparin-minus protein is not retained on this column, and therefore that it no longer has any affinity for heparin. This protein is therefore a heparin-negative mutant.

b. Evaluation of the interaction of the Robo1-Fc protein variants with the D2 domain of the human Slit2 protein This example describes the interaction of the two variants called Robo1-Fc L1 and Robo1-Fc L2 with their natural ligand (in these experiments, the D2 domain of human Slit2) by ELISA assay.

Figure 2:
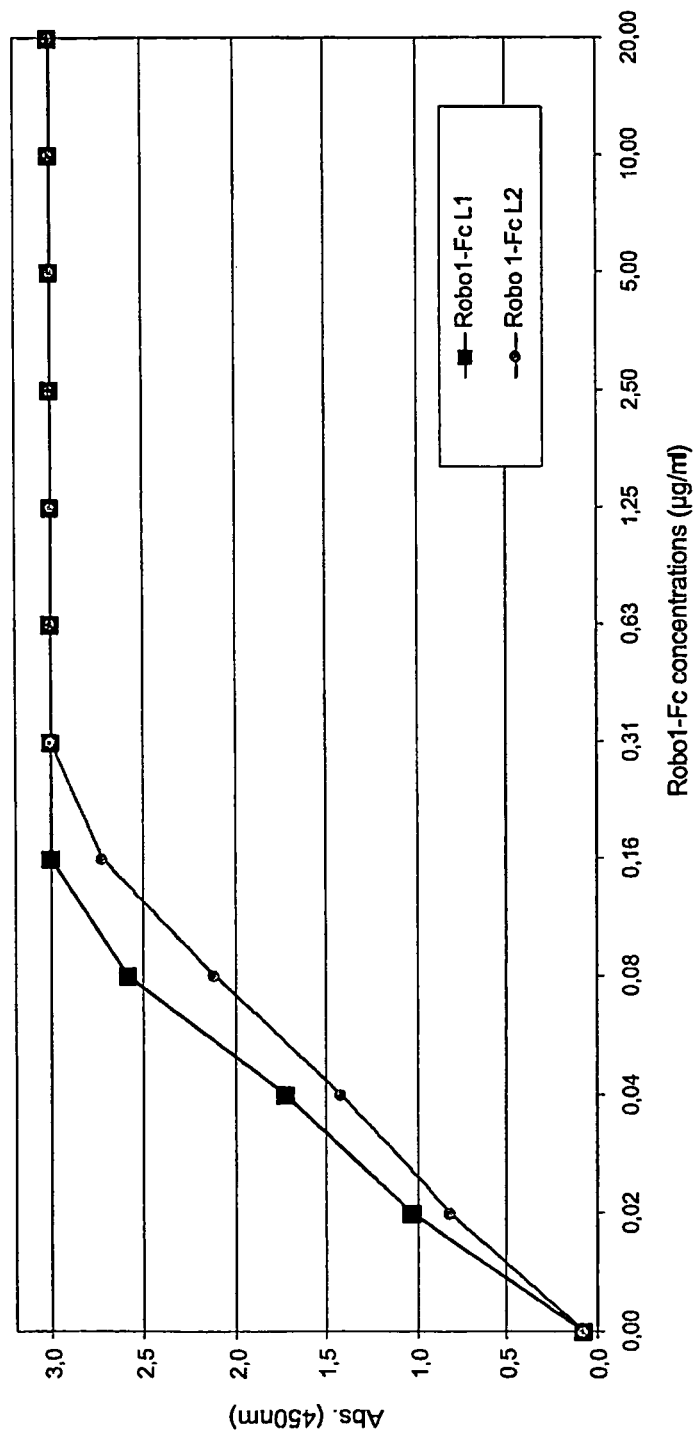
FIG. 2: Evaluation of the interaction of the Robo1-Fc fusion protein variants with the Slit2 protein by ELISA.

The human Slit2-D2 protein was bound to Immulon-4 enzyme-linked plates (VWR Scientific Inc. Swedesboro, N.J.). A concentration range (from 20 µg/mL to 0.02 µg/mL) of the Robo1-Fc L1 and Robo1-Fc L2 variants was added and then detected by means of the peroxidase-conjugated goat anti-human IgG antibody (Sigma; ref. A0170, dilution to 1:50 000). Visualization was carried out with the TMB-$H_2O_2$ substrate (Interchim; ref UP664780) and the measurements were carried out with a plate reader at 450 nm. The results are reported in FIG. 2. They show that the two variants Robo1-Fc L1 and L2 specifically interact with the human Slit2 protein (in particular with the D2 domain).

c. Evaluation of the interaction of the Robo1-Fc protein with the human variants of the Slit family, namely Slit1 and Slit3

This example describes the interaction of the Robo1-Fc L1 fusion protein with the Slit1-D2, Slit2-D2 and Slit3-D2 variants by ELISA assay.

The D2 domain of the human Slit variants was bound to Immulon-4 enzyme-linked plates (VWR Scientific Inc. Swedesboro, N.J.). A concentration range (from 1 µg/mL to 0.001 µg/mL) of the Robo1-Fc L1 fusion protein was added and than detected using the peroxidase-conjugated goat anti-human IgG antibody (Sigma; ref. A0170, dilution to 1:50 000). Visualization was carried out with the TMB-$H_2O_2$ substrate (Interchim; ref UP664780) and the measurements were carried out with a plate reader at 450 nm. Similarly, the Robo1-Fc Slit2-minus variant, which is mutated at the level of the Slit2-binding site, was evaluated according to a concentration range (from 20 µg/mL to 0.02 µg/mL) by ELISA assay under the same conditions described above. The results are reported in table 3 below.

TABLE 3

Affinity of Robo1-Fc for the human variants of the Slit protein

| Slit protein (ligand) | Robo1-Fc protein | EC50 (µg/mL) | CV (%) |
|---|---|---|---|
| Slit2-D2 | Robo1-Fc L1 | 1.32E−01 | 3.3 |
| Slit1-D2 | Robo1-Fc L1 | 7.88E−02 | 3.9 |
| Slit3-D2 | Robo1-Fc L1 | 2.60E−01 | 12 |
| Slit2-D2 | Robo1-Fc Slit2-minus | 1.78E+01 | 18 |

These results show that the Robo1-Fc protein interacts specifically with the three proteins of the family, Slit1, Slit2 and Slit3 (in particular with their D2 domain).

In addition, the Robo1-Fc Slit2-minus protein no longer has affinity for heparin and it is therefore a heparin-negative mutant.

d. Evaluation of the interaction of the Robo1-Fc protein with the murine Slit2 protein This example describes the interaction of the Robo1-Fc L1 fusion protein with the murine protein mSlit2-D2 by ELISA assay.

The murine protein mSlit2-D2 was bound to an Immulon-4 enzyme-linked plate (VWR Scientific Inc. Swedesboro, N.J.). A concentration range (from 2 µg/mL to 0.002 µg/mL) of the Robo1-Fc L1 fusion protein was added and then detected using the peroxidase-conjugated goat anti-human IgG antibody (Sigma; ref. A0170, dilution to 1:50 000). Visualization was carried out with the TMB-$H_2O_2$ substrate (Interchim; ref UP664780) and the measurements were carried out with a plate reader at 450 nm. The results are reported in table 4 below.

TABLE 4

Affinity of Robo1-Fc L1 for the murine Slit2 protein

| Protein studied | EC50 (µg/mL) | CV (%) |
|---|---|---|
| mSlit2-D2 | 2.21E−01 | 18 |

These results show that the Robo1-Fc protein interacts specifically with the murine Slit2 protein e. Affinity of Robo1-Fc for the Slit protein measured by SPR This example describes the determination of the affinity constant of the Robo1-Fc L1 fusion protein with the human Slit2 protein (in this experiment, Slit2-D2) by SPR (Surface Plasmon Resonance; BIAcore 2000). The interaction between the Robo1-Fc protein and the human Slit2 protein was analysed after having bound the Robo1-Fc fusion protein to a CM5 chip. The kinetic measurements were carried out according to the protocol of Canziani et al. (2004. Anal, Biochem. 325: 301-307).

TABLE 5

Affinity constant of Robo-Fc L1 with human Slit2-D2 by SPR (steady-state analysis)

| Protein | $K_D$ (nM) |
|---|---|
| Robo1-Fc L1 | 32 |

A second method, which consists in determining the affinity constant between the Robo1-Fc L1 fusion protein and the human Slit2 protein, was analysed after having bound the Slit2-D2 protein to the CM5 chip. The kinetic measurements are carried out according to the protocol of Canziani et al. (2004. Anal. Biochem. 325: 301-307) using the Scatchard method according to a model with two non-equivalent binding sites,

TABLE 6

Affinity constant of Robo1-Fc with human Slit2-D2 by SPR according to the two-phase Scatchard model

| Robo1-Fc L1 | $K_D$ (nM) |
|---|---|
| High-affinity site | $K_{D1}$: 1.5 |
| Low-affinity site | $K_{D2}$: 160 | f. Affinity of Robo1-Fc for Slit measured by FACS

This example describes the affinity of the Robo1-Fc protein on HEK293 mammalian cells expressing Slit2.

The HEK293 cells described and used as in example 1 were transfected either with a ballast plasmid, having no cDNA that encodes in the mammalian cell, or the pXL4911 plasmid encoding the Slit2-D2 protein, or the pXL4912 plasmid encoding the Slit2-D1D2 protein, or pXL5033 encoding the Slit2-N protein described in example 2, The cells were distributed into 96-well plates 48 hours post-transfection, and the Robo1-Fc protein was added in a concentration range of from 0.01 to 3 mg/L for 30 min at 4° C. The Robo1-Fc protein is either the Robo1-Fc L1 biotherapeutic agent, or the Robo1-Fc Slit2-minus mutant, or the Robo1-Fc heparin-minus mutant. The cells were washed and the anti-human Fc antibody labelled with Alexa 488 (ref: A-11013, Invitrogen) was incubated for 30 min at 4° C. The labelled HEK293 cells are then quantified by FACS (Geomean).

Figure 3:
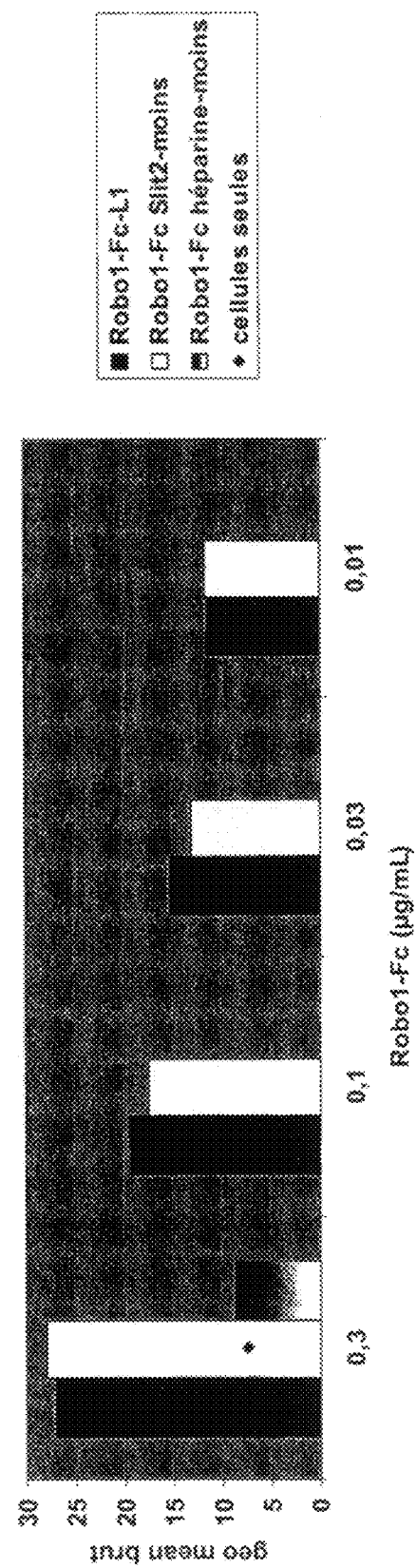
FIG. 3: Affinity of Robo1-Fc for HEK293 cells not expressing Slit2, measured by FACS.

FIG. 3 describes the binding of the HEK293 cells to the Robo1-Fc protein, via the fluorescence measured by the FACS in the absence of Slit2 expression. The Robo1-Fc protein and also the Robo1-Fc Slit2-minus mutant bind to the HEK293 cells, whereas the Robo1-Fc heparin-minus mutant does not bind. Robo1-Fc therefore binds partly to the HEK293 cells via heparin binding at the low Robo1-Fc concentrations of 0.3 to 0.03 mg/L.

Figure 4:
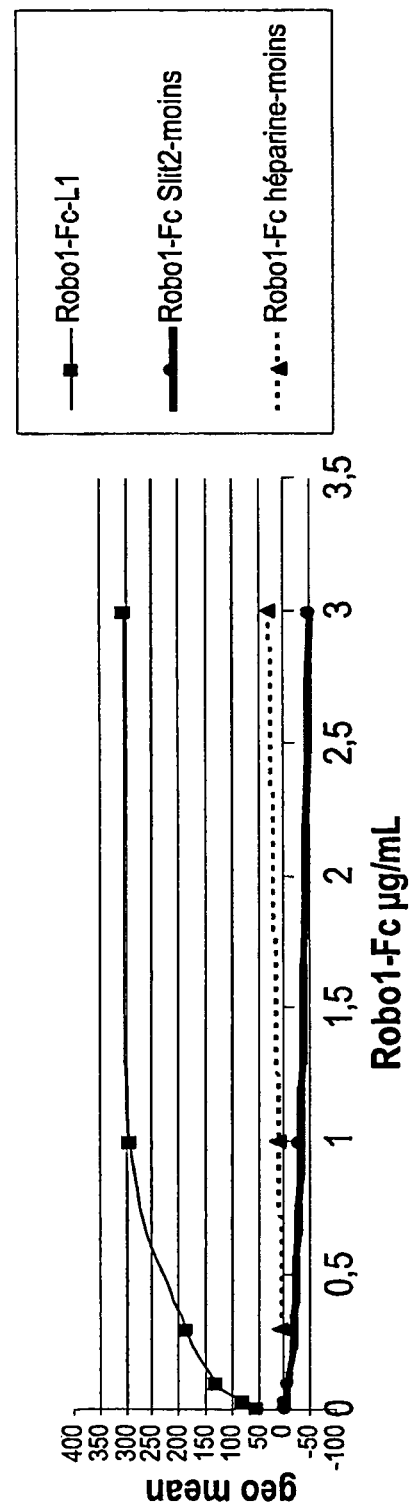
FIG. 4: Affinity of Robo1-Fc for HEK293 cells expressing Slit2, measured by FACS.

FIG. 4 describes the binding of the HEK293 cells to the Robo1-Fc protein, via the fluorescence measured by FACS when Slit2-N is expressed by transient transfection. Only the Robot-Fc protein binds to the HEK293 cells expressing Slit2-N. The Robo1-Fc Slit2-minus and Robot-Fc heparin-minus mutants do not bind (or virtually not) in the Robo1-Fc concentration range of 3.0 to 0.3 mg/L, compared with the biotherapeutic Robo1-Fc L1 protein.

Table 7 describes the affinity constants measured by FACS for the Robo1-Fc protein when the Slit2-N, Slit2-D1D2 or Slit2-D2 proteins are expressed in the HEK293 line.

TABLE 7

Affinity of Robo1-Fc for the Slit2 protein on cells by FACS

| Ligand Robo1-Fc | Protein expressed transiently in HEK293 | $K_D$ (nM) |
| --- | --- | --- |
| Robo1-Fc L1 | Slit2-N | 1.2 |
|  | Slit2-D1D2 | 0.98 |
|  | Slit2-D2 | Very weak binding |
| Robo1-Fc Heparin-minus | Slit2-N | 43 |
|  | Slit2-D1D2 | 41 |
| Robo1-Fc Slit2-minus | Slit2-N | No binding |

As in the previous examples, the Robo1-Fc Slit2-minus mutant proved to be Slit2-negative and the Robo1-Fc heparin-minus mutant has a weaker affinity for Slit2 than the biotherapeutic protein.

Robo1-Fc binds to Slit2-N and Slit2-D1D2 expressed by the HEK293 cells with comparable affinities which are better than the affinity with Slit2-D2.

Example 4

Pharmacokinetic Properties of the Robo1-Fc L1 and Robo1-Fc L2 Proteins

This example describes the pharmacokinetic profile and the plasma concentration of the Robo1-Fc protein injected once in mice intravenously (iv).

Three Balb/C mice (for each time) were injected, via the caudal vein, with each of the Robo1-Fc proteins at 2.5 mg/mL in a proportion of 100 μL/10 g (≈25 mg/kg). At the predetermined times (0.5, 1, 6, 24, 48 and 72 h after administration), the mice were anaesthetized, and blood was sampled and collected in a tube containing 10 μL of citrate (CPD-A, C-4431 Sigma) and 2 of protease inhibitors (Complete Protease Inhibitor Mix, Roche Molecular Biochemical). The tubes were centrifuged and the plasma samples were collected and frozen at −20° C.

The wells of 96-well plates were coated with the Slit2 protein (Slit2-D2), and the plasma samples, diluted to 1/5000 and 1/20 000, were brought into contact for one hour at 37° C. The peroxidase-conjugated anti-human Fc antibody (ref. 31413, Pierce) was subsequently incubated and then visualized with TMB-$H_2O_2$ (ref UP664780, Interchim) and the absorbance was read at 450 nm. A calibration range was prepared with each purified Robo1-Fc protein.

The plasma concentrations of the Robo1-Fc L1 and Robo1-Fc L2 proteins are represented in FIG. 5. The pharmacokinetic parameters are described in the following table 8 and show that the protein is stable after injection in mice.

TABLE 8

Pharmacokinetic parameters of the Robo1-Fc proteins after iv injection in mice

| Protein at 25 mg/kg | $C_0$ μg/mL | $T_{1/2}$ h | AUC (0-last) μg · h/mL | AUC (0-24 h) μg · h/mL | Cl mL/H/kg | Vdss mL/kg |
| --- | --- | --- | --- | --- | --- | --- |
| Robo1-Fc L1 | 203 | 158 | 3655 | 1879 | 2.2 | 470 |
| Robo1-Fc L2 | 198 | 142 | 3973 | 2042 | 2.2 | 417 |

Example 5

Description of the Robo1-Fc Biotherapeutic Protein Improved with Respect to its Homogeneity in the N-Terminal Position This example describes the expression plasmid, the production and the physicochemical characterization of another Robo1-Fc protein, called Robo1-Fc L3, which is different from the Robo1-Fc L1 protein by virtue of the absence of the first two residues Ser20 and Arg21.

The cDNA cloned into the pXL4904 plasmid was modified by PCR in order to eliminate the Ser20 and Arg21 codons, and to fuse the next codon (Leu22) to the coding sequence of the peptide signal of interleukin 2. The pXL5004 expression plasmid was then generated, see FIG. 1. The cDNA sequence used to express this recombinant protein corresponds to the sequence SEQ ID NO. 23.

The Robo1-Fc L3 protein was produced, purified and characterized as described in example 1. The N-terminal analysis showed that this purified protein was perfectly homogeneous. The recombinant protein obtained is called Robo1-Fc L3 and corresponds to the protein sequence SEQ ID NO. 24.

Example 6

Evaluation of the Interaction of the Robo1-Fc L3 Protein with the Human Slit2 Protein This example describes the interaction of the Robo1-Fc L3 fusion protein with the human Slit2 protein (Slit2-D2) by ELISA assay.

The human Slit2-D2 protein was bound to Immulon-4 enzyme-linked plates (VWR Scientific Inc. Swedesboro, N.J.). A concentration range (from 1 µg/mL to 0.001 µg/mL) of the Robot-Fc L3 fusion protein was added and then detected by means of the peroxidase-conjugated goat anti-human IgG antibody (Sigma; ref. A0170, dilution to 1:50 000). The visualization was carried out with the TMB-$H_2O_2$ substrate (Interchim; ref UP664780) and the measurements were carried out with a plate reader at 450 nm. The results obtained are reported in table 9 below.

TABLE 9

Affinity of the Robo1-Fc L3 protein for the Slit2 protein - Comparison with the Robo1-Fc L1 protein

| Proteins studied | EC50 (µg/ml) | CV (%) |
| --- | --- | --- |
| Robo1-Fc L1 | 0.13 | 3.3 |
| Robo1-Fc L3 | 0.17 | 4.4 |

These results show that the affinities of the two variants Robo1-Fc L1 and Robo1-Fc L3 for the Slit2-D2 protein are comparable.

Example 7

Evaluation of the Activity of the Robo-Fc Protein on Neovascularization a. In vitro endothelial cell and fibroblast coculture model: specific activity of the Robo1-Fc L1 molecule The in vitro angiogenesis model corresponds to a rearrangement of human vein endothelial cells on a monolayer of human dermal fibroblasts. Briefly, the fibroblasts (Lonza) are seeded into 24-well plates (Becton Dickinson) at 40 000 cells/well in 1 ml of medium. After 3 days of proliferation (D3), human vein endothelial cells (HUVEC-Lonza) are seeded onto the fibroblast cell monolayer at 10 000 cells/well in 500 µl of EGM® medium (endothelial basal medium, Lonza)+2% FCS (foetal calf serum–Lonza)+10 µg/ml hEGF (recombinant human epidermal growth factor–Lonza). The cells are stimulated with 30 ng/mL of VEGF (R&D Systems), with the Robo1-Fc L1 molecule or with a Robo1-Fc Slit2-minus negative control at the concentration of 500 µg/ml (D3 to D9). After 3 days, the medium is replaced and the wells are stimulated according to the conditions of the experiment.

After 2 days, the cells are fixed with ethanol and labelled with an anti-CD31 antibody specific for HUVECs, followed by an anti-alkaline phosphatase antibody, and then visualized with an alkaline phosphatase substrate (D11). A quantification of the tubules labelled with the anti-CD31 antibody is carried out by means of image acquisitions made under a microscope (×4 objective) and the length of the pseudotubules is analysed using image analysis software (Biocom Visiolab 2000 software) (FIG. 6).

In this in vitro angiogenesis assay, Robo1-Fc L1 (500 µg/ml) shows an inhibitory activity on the formation of the tubules formed by the HUVECs. This inhibition amounts to 82% and it is statistically significant compared with the effect obtained with the Robo1-Fc Slit2-minus molecule (negative control).

b. Ex vivo mouse aortic ring model: specific activity of the Robo1-Fc L1 molecule The Robo1-Fc L1 molecule was evaluated in a mouse aortic ring model. Briefly, mouse aortas are removed and cleaned, and cut into sections of 1 mm (D0). These rings are embedded in rat collagen in the presence of VEGF at 10 ng/ml, of the Robo1-Fc L1 molecule at the concentration of 500 µg/ml or of a Robo1-Fc Slit2-minus negative control at the concentration of 500 µg/ml. Tubules will form from the ring, thus mimicking in vitro, the formation of neovessels. After 6 days, a quantification of the labelled tubules is carried out by means of image acquisitions made under a microscope (×3 objective) (FIG. 7A) and the length of the pseudotubules is analysed using image analysis software (Biocom Visiolab software 2000) (FIG. 7).

Under these experimental conditions, Robo1-Fc L1 (500 µg/ml) shows a strong inhibitory activity on the formation of the tubules formed, in comparison with the Robo1-Fc Slit2-minus molecule used as a negative control.

These results suggest that Robo1-Fc L1 is capable of inhibiting the formation of neovessels without inhibiting endothelial cell proliferation. This anti-angiogenic activity linked to a vessel maturation defect is called "non-productive angiogenesis".

Example 8

Evaluation of the Robo1-Fc L1 Protein in a Lung Tumour Model in Mice

The Robo1-Fc L1 molecule was evaluated in a model of a lung cancer tumour in 057/816 mice.

a. Murine lung tumour model

In order to establish the murine lung tumour model, 8-week-old female C57/BI6 mice were anaesthetized. The area at the level of the left scapula of the mouse was shaved and disinfected. A 1 cm incision was made above the scapula.

The cells to be injected are derived from a Lewis lung carcinoma tumour line (ATCC, CRL-1642). The cells were mixed with Matrigel® in a ratio of 1 vol of Matrigel to 4 vol of cells. The cell concentration was 62 500 cells/ml. The cells were injected into the lung at a rate of 20 µl per mouse, and then the wound was sutured.

After 23 days, the mice were euthanized. The ribcage was opened up, and the left lung and the mediastinal lymph nodes were removed. The tumour present on the left lung was measured using an electronic calliper rule in order to determine the tumour volume according to the formula: I2×L×0.52. The mediastinal lymph nodes are weighed. The results are expressed as mean value±standard deviation from the mean. The statistical analysis was carried out by means of a parametric Student's test.

b. Treatment of the mice bearing a lung tumour with the Robo1-Fc recombinant protein The treatment using the Robo1-Fc protein was carried out as follows: a preparation containing the Robo1-Fc protein was injected at the dose of 25 mg/kg/day, intravenously, on D10, D14, D17 and D21 post-injection of the tumour cells. The control group was injected with PBS buffer (10 ml/kg).

c. Results

On D23, the mean volume of the tumours obtained in the group treated with the Robo1-Fc recombinant protein was 21.45±2.16 mm$^3$; the mean volume of the tumours obtained in the control group was 3993±8.41 mm$^3$. The reduction in tumour volume in the animals treated with the Robo1-Fc protein is 46%. This difference is statistically significant (p<0.05). The mean weight of the mediastinal lymph nodes (metastatic lymph nodes) obtained in the group treated with the Robo1-Fc protein is 12.50±1.25 mg. The mean weight of the mediastinal lymph nodes obtained in the control group is 30.67±7.69 mg. The reduction in weight of the mediastinal lymph nodes for the group treated with the Robo1-Fc protein is 59% at the limit of significance (p=0.07).

We claim:

1. A homogeneous composition of Robo-Fc recombinant protein comprising the extracellular region of a Robo1 protein, a linker and an immunoglobulin Fc domain,
   wherein said extracellular region of the Robo1 protein consists of the Ig1 and Ig2 immunoglobulin domains corresponding to amino acids 22-220 of SEQ ID NO: 2,
   wherein the immunoglobulin Fc domain is from human immunoglobulin G4 and comprises S241P and L248E mutations (Kabat numbering), and wherein the lysine located in the C-terminal position is absent.

2. The homogeneous composition of Robo-Fc recombinant protein according to claim 1, wherein the sequence has at least 80% identity with the sequence of SEQ ID NO: 4, SEQ ID NO: 6 or SEQ ID NO: 24.

3. A pharmaceutical composition comprising the homogeneous composition of Robo-Fc recombinant protein of claim 1.

4. A method for treating a cancer associated with overexpression of a protein of the Slit family comprising administering to a subject in need thereof the pharmaceutical composition of claim 3.

5. The method of claim 4, wherein the cancer is lung cancer or lung metastases.

6. The pharmaceutical composition according to claim 3 further comprising at least one excipient.

7. A method for detecting overexpression of a molecule of the Slit family in a patient comprising contacting a biological sample from the patient with the homogeneous composition of Robo-Fc recombinant protein of claim 1.

8. The homogeneous composition of Robo-Fc recombinant protein according to claim 1, which is produced by transfection of expression plasmid encoding a protein having the amino acid sequence of SEQ ID NO: 4, SEQ ID NO: 6 or SEQ ID NO: 24 into CHO cell, recovery in culture supernatant and purification.

9. The homogeneous composition of Robo-Fc recombinant protein according to claim 1, wherein the Robo-Fc recombinant protein consists of amino acids 22 to 454 of SEQ ID NO: 4.

10. The homogeneous composition of Robo-Fc recombinant protein according to claim 1, wherein the Robo-Fc recombinant protein consists of amino acids 22 to 453 of SEQ ID NO: 6.

11. The homogeneous composition of Robo-Fc recombinant protein according to claim 1, wherein the Robo-Fc recombinant protein consists of amino acids 21 to 453 of SEQ ID NO: 24.

* * * * *

SEQUENCE LISTING

<160> NUMBER OF SEQ ID NOS: 24

<210> SEQ ID NO 1
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 1

| | | | | | | | | | | | | | | | | |
|---|---|---|---|---|---|---|---|---|---|---|---|---|---|---|---|---|
| atg | att | gcg | gag | ccc | gct | cac | ttt | tac | ctg | ttt | gga | tta | ata | tgt | ctc | 48 |
| Met | Ile | Ala | Glu | Pro | Ala | His | Phe | Tyr | Leu | Phe | Gly | Leu | Ile | Cys | Leu | |
| 1 | | | | 5 | | | | | 10 | | | | | 15 | | |
| tgt | tca | ggc | tcc | cgt | ctt | cgt | cag | gaa | gat | ttt | cca | cct | cgc | att | gtt | 96 |
| Cys | Ser | Gly | Ser | Arg | Leu | Arg | Gln | Glu | Asp | Phe | Pro | Pro | Arg | Ile | Val | |
| | | | 20 | | | | | 25 | | | | | 30 | | | |
| gaa | cac | cct | tca | gac | ctg | att | gtc | tca | aaa | gga | gaa | cct | gca | act | ttg | 144 |
| Glu | His | Pro | Ser | Asp | Leu | Ile | Val | Ser | Lys | Gly | Glu | Pro | Ala | Thr | Leu | |
| | | 35 | | | | | 40 | | | | | 45 | | | | |
| aac | tgc | aaa | gct | gaa | ggc | cgc | ccc | aca | ccc | act | att | gaa | tgg | tac | aaa | 192 |
| Asn | Cys | Lys | Ala | Glu | Gly | Arg | Pro | Thr | Pro | Thr | Ile | Glu | Trp | Tyr | Lys | |
| 50 | | | | | 55 | | | | | 60 | | | | | | |
| ggg | gga | gag | aga | gtg | gag | aca | gac | aaa | gat | gac | cct | cgc | tca | cac | cga | 240 |
| Gly | Gly | Glu | Arg | Val | Glu | Thr | Asp | Lys | Asp | Asp | Pro | Arg | Ser | His | Arg | |
| 65 | | | | | 70 | | | | | 75 | | | | | 80 | |
| atg | ttg | ctg | ccg | agt | gga | tct | tta | ttt | ttc | tta | cgt | ata | gta | cat | gga | 288 |
| Met | Leu | Leu | Pro | Ser | Gly | Ser | Leu | Phe | Phe | Leu | Arg | Ile | Val | His | Gly | |
| | | | | 85 | | | | | 90 | | | | | 95 | | |
| cgg | aaa | agt | aga | cct | gat | gaa | gga | gtc | tat | gtc | tgt | gta | gca | agg | aat | 336 |
| Arg | Lys | Ser | Arg | Pro | Asp | Glu | Gly | Val | Tyr | Val | Cys | Val | Ala | Arg | Asn | |
| | | | 100 | | | | | 105 | | | | | 110 | | | |
| tac | ctt | gga | gag | gct | gtg | agc | cac | aat | gca | tcg | ctg | gaa | gta | gcc | ata | 384 |
| Tyr | Leu | Gly | Glu | Ala | Val | Ser | His | Asn | Ala | Ser | Leu | Glu | Val | Ala | Ile | |
| | | 115 | | | | | 120 | | | | | 125 | | | | |
| ctt | cgg | gat | gac | ttc | aga | caa | aac | cct | tcg | gat | gtc | atg | gtt | gca | gta | 432 |
| Leu | Arg | Asp | Asp | Phe | Arg | Gln | Asn | Pro | Ser | Asp | Val | Met | Val | Ala | Val | |
| 130 | | | | | 135 | | | | | 140 | | | | | | |
| gga | gag | cct | gca | gta | atg | gaa | tgc | caa | cct | cca | cga | ggc | cat | cct | gag | 480 |
| Gly | Glu | Pro | Ala | Val | Met | Glu | Cys | Gln | Pro | Pro | Arg | Gly | His | Pro | Glu | |
| 145 | | | | | 150 | | | | | 155 | | | | | 160 | |
| ccc | acc | att | tca | tgg | aag | aaa | gat | ggc | tct | cca | ctg | gat | gat | aaa | gat | 528 |
| Pro | Thr | Ile | Ser | Trp | Lys | Lys | Asp | Gly | Ser | Pro | Leu | Asp | Asp | Lys | Asp | |
| | | | | 165 | | | | | 170 | | | | | 175 | | |
| gaa | aga | ata | act | ata | cga | gga | gga | aag | ctc | atg | atc | act | tac | acc | cgt | 576 |
| Glu | Arg | Ile | Thr | Ile | Arg | Gly | Gly | Lys | Leu | Met | Ile | Thr | Tyr | Thr | Arg | |
| | | | 180 | | | | | 185 | | | | | 190 | | | |
| aaa | agt | gac | gct | ggc | aaa | tat | gtt | tgt | gtt | ggt | acc | aat | atg | gtt | ggg | 624 |
| Lys | Ser | Asp | Ala | Gly | Lys | Tyr | Val | Cys | Val | Gly | Thr | Asn | Met | Val | Gly | |
| | | 195 | | | | | 200 | | | | | 205 | | | | |
| gaa | cgt | gag | agt | gaa | gta | gcc | gag | ctg | act | gtc | tta | | | | | 660 |
| Glu | Arg | Glu | Ser | Glu | Val | Ala | Glu | Leu | Thr | Val | Leu | | | | | |
| | 210 | | | | | 215 | | | | | 220 | | | | | |

<210> SEQ ID NO 2
<211> LENGTH: 220
<212> TYPE: PRT
<213> ORGANISM: Homo sapiens

<400> SEQUENCE: 2

Met Ile Ala Glu Pro Ala His Phe Tyr Leu Phe Gly Leu Ile Cys Leu
1               5                   10                  15

```
Cys Ser Gly Ser Arg Leu Arg Gln Glu Asp Phe Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
 50                  55                  60

Gly Gly Glu Arg Val Glu Thr Asp Lys Asp Asp Pro Arg Ser His Arg
 65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Val Cys Val Ala Arg Asn
            100                 105                 110

Tyr Leu Gly Glu Ala Val Ser His Asn Ala Ser Leu Glu Val Ala Ile
        115                 120                 125

Leu Arg Asp Asp Phe Arg Gln Asn Pro Ser Asp Val Met Val Ala Val
    130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
        195                 200                 205

Glu Arg Glu Ser Glu Val Ala Glu Leu Thr Val Leu
    210                 215                 220

<210> SEQ ID NO 3
<211> LENGTH: 1365
<212> TYPE: DNA
<213> ORGANISM: Homo sapiens
<220> FEATURE:
<221> NAME/KEY: CDS
<222> LOCATION: (1)..(1365)

<400> SEQUENCE: 3 atg att gcg gag ccc gct cac ttt tac ctg ttt gga tta ata tgt ctc      48
Met Ile Ala Glu Pro Ala His Phe Tyr Leu Phe Gly Leu Ile Cys Leu
 1               5                  10                  15 tgt tca ggc tcc cgt ctt cgt cag gaa gat ttt cca cct cgc att gtt      96
Cys Ser Gly Ser Arg Leu Arg Gln Glu Asp Phe Pro Pro Arg Ile Val
            20                  25                  30 gaa cac cct tca gac ctg att gtc tca aaa gga gaa cct gca act ttg     144
Glu His Pro Ser Asp Leu Ile Val Ser Lys Gly Glu Pro Ala Thr Leu
        35                  40                  45 aac tgc aaa gct gaa ggc cgc ccc aca ccc act att gaa tgg tac aaa     192
Asn Cys Lys Ala Glu Gly Arg Pro Thr Pro Thr Ile Glu Trp Tyr Lys
 50                  55                  60 ggg gga gag aga gtg gag aca gac aaa gat gac cct cgc tca cac cga     240
Gly Gly Glu Arg Val Glu Thr Asp Lys Asp Asp Pro Arg Ser His Arg
 65                  70                  75                  80 atg ttg ctg ccg agt gga tct tta ttt ttc tta cgt ata gta cat gga     288
Met Leu Leu Pro Ser Gly Ser Leu Phe Phe Leu Arg Ile Val His Gly
                85                  90                  95 cgg aaa agt aga cct gat gaa gga gtc tat gtc tgt gta gca agg aat     336
Arg Lys Ser Arg Pro Asp Glu Gly Val Tyr Val Cys Val Ala Arg Asn
            100                 105                 110
```

| | | |
|---|---|---|
| tac ctt gga gag gct gtg agc cac aat gca tcg ctg gaa gta gcc ata<br>Tyr Leu Gly Glu Ala Val Ser His Asn Ala Ser Leu Glu Val Ala Ile<br>115 120 125 | | 384 |
| ctt cgg gat gac ttc aga caa aac cct tcg gat gtc atg gtt gca gta<br>Leu Arg Asp Asp Phe Arg Gln Asn Pro Ser Asp Val Met Val Ala Val<br>130 135 140 | | 432 |
| gga gag cct gca gta atg gaa tgc caa cct cca cga ggc cat cct gag<br>Gly Glu Pro Ala Val Met Glu Cys Gln Pro Pro Arg Gly His Pro Glu<br>145 150 155 160 | | 480 |
| ccc acc att tca tgg aag aaa gat ggc tct cca ctg gat gat aaa gat<br>Pro Thr Ile Ser Trp Lys Lys Asp Gly Ser Pro Leu Asp Asp Lys Asp<br>165 170 175 | | 528 |
| gaa aga ata act ata cga gga gga aag ctc atg atc act tac acc cgt<br>Glu Arg Ile Thr Ile Arg Gly Gly Lys Leu Met Ile Thr Tyr Thr Arg<br>180 185 190 | | 576 |
| aaa agt gac gct ggc aaa tat gtt tgt gtt ggt acc aat atg gtt ggg<br>Lys Ser Asp Ala Gly Lys Tyr Val Cys Val Gly Thr Asn Met Val Gly<br>195 200 205 | | 624 |
| gaa cgt gag agt gaa gta gcc gag ctg act gtc tta gag aga cca tca<br>Glu Arg Glu Ser Glu Val Ala Glu Leu Thr Val Leu Glu Arg Pro Ser<br>210 215 220 | | 672 |
| ttt gtg gag tcc aag tac ggc cct cct tgc cct ccc tgc cct gcc cct<br>Phe Val Glu Ser Lys Tyr Gly Pro Pro Cys Pro Pro Cys Pro Ala Pro<br>225 230 235 240 | | 720 |
| gag ttc gag ggc gga cct agc gtg ttc ctg ttc cct cct aag cct aag<br>Glu Phe Glu Gly Gly Pro Ser Val Phe Leu Phe Pro Pro Lys Pro Lys<br>245 250 255 | | 768 |
| gac acc ctg atg atc tcc cgg acc cct gag gtg acc tgt gtg gtg gtg<br>Asp Thr Leu Met Ile Ser Arg Thr Pro Glu Val Thr Cys Val Val Val<br>260 265 270 | | 816 |
| gac gtg tcc cag gag gac cct gag gtc cag ttc aac tgg tac gtg gac<br>Asp Val Ser Gln Glu Asp Pro Glu Val Gln Phe Asn Trp Tyr Val Asp<br>275 280 285 | | 864 |
| ggc gtg gag gtg cac aac gcc aag acc aag cct cgg gag gag cag ttc<br>Gly Val Glu Val His Asn Ala Lys Thr Lys Pro Arg Glu Glu Gln Phe<br>290 295 300 | | 912 |
| aat tcc acc tac cgg gtg gtg tct gtg ctg acc gtg ctg cac cag gac<br>Asn Ser Thr Tyr Arg Val Val Ser Val Leu Thr Val Leu His Gln Asp<br>305 310 315 320 | | 960 |
| tgg ctg aac ggc aaa gaa tac aag tgt aag gtc tcc aac aag ggc ctg<br>Trp Leu Asn Gly Lys Glu Tyr Lys Cys Lys Val Ser Asn Lys Gly Leu<br>325 330 335 | | 1008 |
| ccc tcc tcc atc gag aaa acc atc tcc aag gcc aag ggc cag cct agg<br>Pro Ser Ser Ile Glu Lys Thr Ile Ser Lys Ala Lys Gly Gln Pro Arg<br>340 345 350 | | 1056 |
| gag cct cag gtg tac acc ctg cct cct agc cag gaa gag atg acc aag<br>Glu Pro Gln Val Tyr Thr Leu Pro Pro Ser Gln Glu Glu Met Thr Lys<br>355 360 365 | | 1104 |
| aac cag gtg tcc ctg acc tgt ctg gtg aag ggc ttc tac cct tcc gac<br>Asn Gln Val Ser Leu Thr Cys Leu Val Lys Gly Phe Tyr Pro Ser Asp<br>370 375 380 | | 1152 |
| atc gcc gtg gag tgg gag tcc aac ggc cag cct gag aac aac tac aag<br>Ile Ala Val Glu Trp Glu Ser Asn Gly Gln Pro Glu Asn Asn Tyr Lys<br>385 390 395 400 | | 1200 |
| acc acc cct cct gtg ctg gac tcc gac ggc tcc ttc ttc ctg tac tcc<br>Thr Thr Pro Pro Val Leu Asp Ser Asp Gly Ser Phe Phe Leu Tyr Ser<br>405 410 415 | | 1248 |
| agg ctg acc gtg gac aag tcc cgg tgg cag gag ggc aac gtc ttt tcc<br>Arg Leu Thr Val Asp Lys Ser Arg Trp Gln Glu Gly Asn Val Phe Ser<br>420 425 430 | | 1296 |

```
tgc tcc gtg atg cac gag gcc ctg cac aac cac tac acc cag aag tcc    1344
Cys Ser Val Met His Glu Ala Leu His Asn His Tyr Thr Gln Lys Ser
        435                 440                 445 ctg tcc ctg tct ctg ggc tga                                        1365
Leu Ser Leu Ser Leu Gly
    450

<210> SEQ ID NO 4
<211> LENGTH: 454
<212> TYPE: PRT
<213> ORGANISM: Homo sapiens

<400> SEQUENCE: 4

Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Val Cys Val Ala Arg Asn
            100                 105                 110

Tyr Leu Gly Glu Ala Val Ser His Asn Ala Ser Leu Glu Val Ala Ile
        115                 120                 125

Leu Arg Asp Asp Phe Arg Gln Asn Pro Ser Asp Val Met Val Ala Val
    130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
        195                 200                 205

Glu Arg Glu Ser Glu Val Ala Glu Leu Thr Val Leu Glu Arg Pro Ser
    210                 215                 220

Phe Val Glu Ser Lys Tyr Gly Pro Pro Cys Pro Pro Cys Pro Ala Pro
225                 230                 235                 240

Glu Phe Glu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335
```

```
Pro Ser Ser Ile Glu Lys Thr Ile Ser Lys Ala Lys Gly Gln Pro Arg
            340                 345                 350

Glu Pro Gln Val Tyr Thr Leu Pro Ser Gln Glu Met Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Leu Gly
            450

<210> SEQ ID NO 5
<211> LENGTH: 1362
<212> TYPE: DNA
<213> ORGANISM: Homo sapiens
<220> FEATURE:
<221> NAME/KEY: CDS
<222> LOCATION: (1)..(1362)

<400> SEQUENCE: 5 atg att gcg gag ccc gct cac ttt tac ctg ttt gga tta ata tgt ctc      48
Met Ile Ala Glu Pro Ala His Phe Tyr Leu Phe Gly Leu Ile Cys Leu
1               5                  10                  15 tgt tca ggc tcc cgt ctt cgt cag gaa gat ttt cca cct cgc att gtt     96
Cys Ser Gly Ser Arg Leu Arg Gln Glu Asp Phe Pro Pro Arg Ile Val
            20                  25                  30 gaa cac cct tca gac ctg att gtc tca aaa gga gaa cct gca act ttg    144
Glu His Pro Ser Asp Leu Ile Val Ser Lys Gly Glu Pro Ala Thr Leu
        35                  40                  45 aac tgc aaa gct gaa ggc cgc ccc aca ccc act att gaa tgg tac aaa    192
Asn Cys Lys Ala Glu Gly Arg Pro Thr Pro Thr Ile Glu Trp Tyr Lys
    50                  55                  60 ggg gga gag aga gtg gag aca gac aaa gat gac cct cgc tca cac cga    240
Gly Gly Glu Arg Val Glu Thr Asp Lys Asp Asp Pro Arg Ser His Arg
65                  70                  75                  80 atg ttg ctg ccg agt gga tct tta ttt ttc tta cgt ata gta cat gga    288
Met Leu Leu Pro Ser Gly Ser Leu Phe Phe Leu Arg Ile Val His Gly
                85                  90                  95 cgg aaa agt aga cct gat gaa gga gtc tat gtc tgt gta gca agg aat    336
Arg Lys Ser Arg Pro Asp Glu Gly Val Tyr Val Cys Val Ala Arg Asn
            100                 105                 110 tac ctt gga gag gct gtg agc cac aat gca tcg ctg gaa gta gcc ata    384
Tyr Leu Gly Glu Ala Val Ser His Asn Ala Ser Leu Glu Val Ala Ile
        115                 120                 125 ctt cgg gat gac ttc aga caa aac cct tcg gat gtc atg gtt gca gta    432
Leu Arg Asp Asp Phe Arg Gln Asn Pro Ser Asp Val Met Val Ala Val
    130                 135                 140 gga gag cct gca gta atg gaa tgc caa cct cca cga ggc cat cct gag    480
Gly Glu Pro Ala Val Met Glu Cys Gln Pro Pro Arg Gly His Pro Glu
145                 150                 155                 160 ccc acc att tca tgg aag aaa gat ggc tct cca ctg gat gat aaa gat    528
Pro Thr Ile Ser Trp Lys Lys Asp Gly Ser Pro Leu Asp Asp Lys Asp
                165                 170                 175
```

```
gaa aga ata act ata cga gga gga aag ctc atg atc act tac acc cgt      576
Glu Arg Ile Thr Ile Arg Gly Gly Lys Leu Met Ile Thr Tyr Thr Arg
            180                 185                 190 aaa agt gac gct ggc aaa tat gtt tgt gtt ggt acc aat atg gtt ggg      624
Lys Ser Asp Ala Gly Lys Tyr Val Cys Val Gly Thr Asn Met Val Gly
        195                 200                 205 gaa cgt gag agt gaa gta gcc gag ctg act gtc tta gga ggc gga gga      672
Glu Arg Glu Ser Glu Val Ala Glu Leu Thr Val Leu Gly Gly Gly Gly
    210                 215                 220 tcc gag tcc aag tac ggc cct cct tgc cct ccc tgc cct gcc cct gag      720
Ser Glu Ser Lys Tyr Gly Pro Pro Cys Pro Pro Cys Pro Ala Pro Glu
225                 230                 235                 240 ttc gag ggc gga cct agc gtg ttc ctg ttc cct cct aag cct aag gac      768
Phe Glu Gly Gly Pro Ser Val Phe Leu Phe Pro Pro Lys Pro Lys Asp
                245                 250                 255 acc ctg atg atc tcc cgg acc cct gag gtg acc tgt gtg gtg gtg gac      816
Thr Leu Met Ile Ser Arg Thr Pro Glu Val Thr Cys Val Val Val Asp
            260                 265                 270 gtg tcc cag gag gac cct gag gtc cag ttc aac tgg tac gtg gac ggc      864
Val Ser Gln Glu Asp Pro Glu Val Gln Phe Asn Trp Tyr Val Asp Gly
        275                 280                 285 gtg gag gtg cac aac gcc aag acc aag cct cgg gag gag cag ttc aat      912
Val Glu Val His Asn Ala Lys Thr Lys Pro Arg Glu Glu Gln Phe Asn
    290                 295                 300 tcc acc tac cgg gtg gtg tct gtg ctg acc gtg ctg cac cag gac tgg      960
Ser Thr Tyr Arg Val Val Ser Val Leu Thr Val Leu His Gln Asp Trp
305                 310                 315                 320 ctg aac ggc aaa gaa tac aag tgt aag gtc tcc aac aag ggc ctg ccc     1008
Leu Asn Gly Lys Glu Tyr Lys Cys Lys Val Ser Asn Lys Gly Leu Pro
                325                 330                 335 tcc tcc atc gag aaa acc atc tcc aag gcc aag ggc cag cct agg gag     1056
Ser Ser Ile Glu Lys Thr Ile Ser Lys Ala Lys Gly Gln Pro Arg Glu
            340                 345                 350 cct cag gtg tac acc ctg cct cct agc cag gaa gag atg acc aag aac     1104
Pro Gln Val Tyr Thr Leu Pro Pro Ser Gln Glu Glu Met Thr Lys Asn
        355                 360                 365 cag gtg tcc ctg acc tgt ctg gtg aag ggc ttc tac cct tcc gac atc     1152
Gln Val Ser Leu Thr Cys Leu Val Lys Gly Phe Tyr Pro Ser Asp Ile
    370                 375                 380 gcc gtg gag tgg gag tcc aac ggc cag cct gag aac aac tac aag acc     1200
Ala Val Glu Trp Glu Ser Asn Gly Gln Pro Glu Asn Asn Tyr Lys Thr
385                 390                 395                 400 acc cct cct gtg ctg gac tcc gac ggc tcc ttc ttc ctg tac tcc agg     1248
Thr Pro Pro Val Leu Asp Ser Asp Gly Ser Phe Phe Leu Tyr Ser Arg
                405                 410                 415 ctg acc gtg gac aag tcc cgg tgg cag gag ggc aac gtc ttt tcc tgc     1296
Leu Thr Val Asp Lys Ser Arg Trp Gln Glu Gly Asn Val Phe Ser Cys
            420                 425                 430 tcc gtg atg cac gag gcc ctg cac aac cac tac acc cag aag tcc ctg     1344
Ser Val Met His Glu Ala Leu His Asn His Tyr Thr Gln Lys Ser Leu
        435                 440                 445 tcc ctg tct ctg ggc tga                                              1362
Ser Leu Ser Leu Gly
    450

<210> SEQ ID NO 6
<211> LENGTH: 453
<212> TYPE: PRT
<213> ORGANISM: Homo sapiens
```

<400> SEQUENCE: 6

```
Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Val Cys Val Ala Arg Asn
                100                 105                 110

Tyr Leu Gly Glu Ala Val Ser His Asn Ala Ser Leu Glu Val Ala Ile
            115                 120                 125

Leu Arg Asp Asp Phe Arg Gln Asn Pro Ser Asp Val Met Val Ala Val
130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
        195                 200                 205

Glu Arg Glu Ser Glu Val Ala Glu Leu Thr Val Leu Gly Gly Gly
210                 215                 220

Ser Glu Ser Lys Tyr Gly Pro Pro Cys Pro Pro Cys Pro Ala Pro Glu
225                 230                 235                 240

Phe Glu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415
```

```
<210> SEQ ID NO 7
<211> LENGTH: 1365
<212> TYPE: DNA
<213> ORGANISM: Homo sapiens
<220> FEATURE:
<221> NAME/KEY: CDS
<222> LOCATION: (1)..(1365)

<400> SEQUENCE: 7
```

| | | | | | | | | | | | | | | | | |
|---|---|---|---|---|---|---|---|---|---|---|---|---|---|---|---|---|
| Leu | Thr | Val | Asp | Lys | Ser | Arg | Trp | Gln | Glu | Gly | Asn | Val | Phe | Ser | Cys | |
| | | | 420 | | | | 425 | | | | 430 | | | | | |
| Ser | Val | Met | His | Glu | Ala | Leu | His | Asn | His | Tyr | Thr | Gln | Lys | Ser | Leu | |
| | | 435 | | | | | 440 | | | | 445 | | | | | |
| Ser | Leu | Ser | Leu | Gly | | | | | | | | | | | | |
| | 450 | | | | | | | | | | | | | | | |

```
atg att gcg gag ccc gct cac ttt tac ctg ttt gga tta ata tgt ctc      48
Met Ile Ala Glu Pro Ala His Phe Tyr Leu Phe Gly Leu Ile Cys Leu
1               5                   10                  15 tgt tca ggc tcc cgt ctt cgt cag gaa gat ttt cca cct cgc att gtt      96
Cys Ser Gly Ser Arg Leu Arg Gln Glu Asp Phe Pro Pro Arg Ile Val
                20                  25                  30 gaa cac cct tca gac cag att gtc tca aaa gga gaa cct gca act ttg     144
Glu His Pro Ser Asp Gln Ile Val Ser Lys Gly Glu Pro Ala Thr Leu
            35                  40                  45 aac tgc aaa gct gaa ggc cgc ccc aca ccc act att gaa tgg tac aaa     192
Asn Cys Lys Ala Glu Gly Arg Pro Thr Pro Thr Ile Glu Trp Tyr Lys
        50                  55                  60 ggg gga gag aga gtg gag aca gac aaa gat gac cct cgc tca cac cga     240
Gly Gly Glu Arg Val Glu Thr Asp Lys Asp Asp Pro Arg Ser His Arg
65                  70                  75                  80 atg ttg ctg ccg agt gga tct tta tat ttc tta cgt ata gta cat gga     288
Met Leu Leu Pro Ser Gly Ser Leu Tyr Phe Leu Arg Ile Val His Gly
                85                  90                  95 cgg aaa agt aga cct gat gaa gga gtc tat gtc tgt gta gca agg aat     336
Arg Lys Ser Arg Pro Asp Glu Gly Val Tyr Val Cys Val Ala Arg Asn
                100                 105                 110 tac ctt gga gag gct gtg agc cac aat gca tcg ctg gaa gta gcc ata     384
Tyr Leu Gly Glu Ala Val Ser His Asn Ala Ser Leu Glu Val Ala Ile
            115                 120                 125 ctt cgg gat gac ttc aga caa aac cct tcg gat gtc atg gtt gca gta     432
Leu Arg Asp Asp Phe Arg Gln Asn Pro Ser Asp Val Met Val Ala Val
        130                 135                 140 gga gag cct gca gta atg gaa tgc caa cct cca cga ggc cat cct gag     480
Gly Glu Pro Ala Val Met Glu Cys Gln Pro Pro Arg Gly His Pro Glu
145                 150                 155                 160 ccc acc att tca tgg aag aaa gat ggc tct cca ctg gat gat aaa gat     528
Pro Thr Ile Ser Trp Lys Lys Asp Gly Ser Pro Leu Asp Asp Lys Asp
                165                 170                 175 gaa aga ata act ata cga gga gga aag ctc atg atc act tac acc cgt     576
Glu Arg Ile Thr Ile Arg Gly Gly Lys Leu Met Ile Thr Tyr Thr Arg
                180                 185                 190 aaa agt gac gct ggc aaa tat gtt tgt gtt ggt acc aat atg gtt ggg     624
Lys Ser Asp Ala Gly Lys Tyr Val Cys Val Gly Thr Asn Met Val Gly
            195                 200                 205 gaa cgt gag agt gaa gta gcc gag ctg act gtc tta gag aga cca tca     672
Glu Arg Glu Ser Glu Val Ala Glu Leu Thr Val Leu Glu Arg Pro Ser
        210                 215                 220 ttt gtg gag tcc aag tac ggc cct cct tgc cct ccc tgc cct gcc cct     720
Phe Val Glu Ser Lys Tyr Gly Pro Pro Cys Pro Pro Cys Pro Ala Pro
```

-continued

```
                 225                 230                 235                 240
gag ttc gag ggc gga cct agc gtg ttc ctg ttc cct cct aag cct aag        768
Glu Phe Glu Gly Gly Pro Ser Val Phe Leu Phe Pro Pro Lys Pro Lys
                 245                 250                 255 gac acc ctg atg atc tcc cgg acc cct gag gtg acc tgt gtg gtg gtg        816
Asp Thr Leu Met Ile Ser Arg Thr Pro Glu Val Thr Cys Val Val Val
             260                 265                 270 gac gtg tcc cag gag gac cct gag gtc cag ttc aac tgg tac gtg gac        864
Asp Val Ser Gln Glu Asp Pro Glu Val Gln Phe Asn Trp Tyr Val Asp
         275                 280                 285 ggc gtg gag gtg cac aac gcc aag acc aag cct cgg gag gag cag ttc        912
Gly Val Glu Val His Asn Ala Lys Thr Lys Pro Arg Glu Glu Gln Phe
     290                 295                 300 aat tcc acc tac cgg gtg gtg tct gtg ctg acc gtg ctg cac cag gac        960
Asn Ser Thr Tyr Arg Val Val Ser Val Leu Thr Val Leu His Gln Asp
305                 310                 315                 320 tgg ctg aac ggc aaa gaa tac aag tgt aag gtc tcc aac aag ggc ctg       1008
Trp Leu Asn Gly Lys Glu Tyr Lys Cys Lys Val Ser Asn Lys Gly Leu
                 325                 330                 335 ccc tcc tcc atc gag aaa acc atc tcc aag gcc aag ggc cag cct agg       1056
Pro Ser Ser Ile Glu Lys Thr Ile Ser Lys Ala Lys Gly Gln Pro Arg
             340                 345                 350 gag cct cag gtg tac acc ctg cct cct agc cag gaa gag atg acc aag       1104
Glu Pro Gln Val Tyr Thr Leu Pro Pro Ser Gln Glu Glu Met Thr Lys
         355                 360                 365 aac cag gtg tcc ctg acc tgt ctg gtg aag ggc ttc tac cct tcc gac       1152
Asn Gln Val Ser Leu Thr Cys Leu Val Lys Gly Phe Tyr Pro Ser Asp
     370                 375                 380 atc gcc gtg gag tgg gag tcc aac ggc cag cct gag aac aac tac aag       1200
Ile Ala Val Glu Trp Glu Ser Asn Gly Gln Pro Glu Asn Asn Tyr Lys
385                 390                 395                 400 acc acc cct cct gtg ctg gac tcc gac ggc tcc ttc ttc ctg tac tcc       1248
Thr Thr Pro Pro Val Leu Asp Ser Asp Gly Ser Phe Phe Leu Tyr Ser
                 405                 410                 415 agg ctg acc gtg gac aag tcc cgg tgg cag gag ggc aac gtc ttt tcc       1296
Arg Leu Thr Val Asp Lys Ser Arg Trp Gln Glu Gly Asn Val Phe Ser
             420                 425                 430 tgc tcc gtg atg cac gag gcc ctg cac aac cac tac acc cag aag tcc       1344
Cys Ser Val Met His Glu Ala Leu His Asn His Tyr Thr Gln Lys Ser
         435                 440                 445 ctg tcc ctg tct ctg ggc tga                                           1365
Leu Ser Leu Ser Leu Gly
     450
```

<210> SEQ ID NO 8
<211> LENGTH: 454
<212> TYPE: PRT
<213> ORGANISM: Homo sapiens

<400> SEQUENCE: 8

```
Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Gln Ile Val Ser Lys Gly Glu Pro Ala Thr Leu
        35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Asp Pro Arg Ser His Arg
```

```
                65                  70                  75                  80
        Met Leu Leu Pro Ser Gly Ser Leu Tyr Phe Leu Arg Ile Val His Gly
                        85                  90                  95

Arg Lys Ser Arg Pro Asp Glu Gly Val Tyr Val Cys Val Ala Arg Asn
                        100                 105                 110

Tyr Leu Gly Glu Ala Val Ser His Asn Ala Ser Leu Glu Val Ala Ile
                        115                 120                 125

Leu Arg Asp Asp Phe Arg Gln Asn Pro Ser Asp Val Met Val Ala Val
                        130                 135                 140

Gly Glu Pro Ala Val Met Glu Cys Gln Pro Pro Arg Gly His Pro Glu
        145                 150                 155                 160

Pro Thr Ile Ser Trp Lys Lys Asp Gly Ser Pro Leu Asp Asp Lys Asp
                        165                 170                 175

Glu Arg Ile Thr Ile Arg Gly Gly Lys Leu Met Ile Thr Tyr Thr Arg
                        180                 185                 190

Lys Ser Asp Ala Gly Lys Tyr Val Cys Val Gly Thr Asn Met Val Gly
                        195                 200                 205

Glu Arg Glu Ser Glu Val Ala Glu Leu Thr Val Leu Glu Arg Pro Ser
                        210                 215                 220

Phe Val Glu Ser Lys Tyr Gly Pro Pro Cys Pro Cys Pro Ala Pro
        225                 230                 235                 240

Glu Phe Glu Gly Gly Pro Ser Val Phe Leu Phe Pro Pro Lys Pro Lys
                        245                 250                 255

Asp Thr Leu Met Ile Ser Arg Thr Pro Glu Val Thr Cys Val Val Val
                        260                 265                 270

Asp Val Ser Gln Glu Asp Pro Glu Val Gln Phe Asn Trp Tyr Val Asp
                        275                 280                 285

Gly Val Glu Val His Asn Ala Lys Thr Lys Pro Arg Glu Glu Gln Phe
                        290                 295                 300

Asn Ser Thr Tyr Arg Val Val Ser Val Leu Thr Val Leu His Gln Asp
        305                 310                 315                 320

Trp Leu Asn Gly Lys Glu Tyr Lys Cys Lys Val Ser Asn Lys Gly Leu
                        325                 330                 335

Pro Ser Ser Ile Glu Lys Thr Ile Ser Lys Ala Lys Gly Gln Pro Arg
                        340                 345                 350

Glu Pro Gln Val Tyr Thr Leu Pro Pro Ser Gln Glu Glu Met Thr Lys
                        355                 360                 365

Asn Gln Val Ser Leu Thr Cys Leu Val Lys Gly Phe Tyr Pro Ser Asp
                        370                 375                 380

Ile Ala Val Glu Trp Glu Ser Asn Gly Gln Pro Glu Asn Asn Tyr Lys
        385                 390                 395                 400

Thr Thr Pro Pro Val Leu Asp Ser Asp Gly Ser Phe Phe Leu Tyr Ser
                        405                 410                 415

Arg Leu Thr Val Asp Lys Ser Arg Trp Gln Glu Gly Asn Val Phe Ser
                        420                 425                 430

Cys Ser Val Met His Glu Ala Leu His Asn His Tyr Thr Gln Lys Ser
                        435                 440                 445

Leu Ser Leu Ser Leu Gly
                450

<210> SEQ ID NO 9
<211> LENGTH: 1365
<212> TYPE: DNA
<213> ORGANISM: Homo sapiens
```

-continued

```
<220> FEATURE:
<221> NAME/KEY: CDS
<222> LOCATION: (1)..(1365)

<400> SEQUENCE: 9
```

| | | | | | | | | | | | | | | | | |
|---|---|---|---|---|---|---|---|---|---|---|---|---|---|---|---|---|
| atg | att | gcg | gag | ccc | gct | cac | ttt | tac | ctg | ttt | gga | tta | ata | tgt | ctc | 48 |
| Met | Ile | Ala | Glu | Pro | Ala | His | Phe | Tyr | Leu | Phe | Gly | Leu | Ile | Cys | Leu | |
| 1 | | | | 5 | | | | | 10 | | | | | 15 | | |
| tgt | tca | ggc | tcc | cgt | ctt | cgt | cag | gaa | gat | ttt | cca | cct | cgc | att | gtt | 96 |
| Cys | Ser | Gly | Ser | Arg | Leu | Arg | Gln | Glu | Asp | Phe | Pro | Pro | Arg | Ile | Val | |
| | | | 20 | | | | | 25 | | | | | 30 | | | |
| gaa | cac | cct | tca | gac | ctg | att | gtc | tca | aaa | gga | gaa | cct | gca | act | ttg | 144 |
| Glu | His | Pro | Ser | Asp | Leu | Ile | Val | Ser | Lys | Gly | Glu | Pro | Ala | Thr | Leu | |
| | | 35 | | | | | 40 | | | | | 45 | | | | |
| aac | tgc | aaa | gct | gaa | ggc | cgc | ccc | aca | ccc | act | att | gaa | tgg | tac | aaa | 192 |
| Asn | Cys | Lys | Ala | Glu | Gly | Arg | Pro | Thr | Pro | Thr | Ile | Glu | Trp | Tyr | Lys | |
| | 50 | | | | | 55 | | | | | 60 | | | | | |
| ggg | gga | gag | aga | gtg | gag | aca | gac | aaa | gat | gac | cct | cgc | tca | cac | cga | 240 |
| Gly | Gly | Glu | Arg | Val | Glu | Thr | Asp | Lys | Asp | Asp | Pro | Arg | Ser | His | Arg | |
| 65 | | | | | 70 | | | | | 75 | | | | | 80 | |
| atg | ttg | ctg | ccg | agt | gga | tct | tta | ttt | ttc | tta | cgt | ata | gta | cat | gga | 288 |
| Met | Leu | Leu | Pro | Ser | Gly | Ser | Leu | Phe | Phe | Leu | Arg | Ile | Val | His | Gly | |
| | | | | 85 | | | | | 90 | | | | | 95 | | |
| gcc | gcc | agt | aga | cct | gat | gaa | gga | gtc | tat | gtc | tgt | gta | gca | agg | aat | 336 |
| Ala | Ala | Ser | Arg | Pro | Asp | Glu | Gly | Val | Tyr | Val | Cys | Val | Ala | Arg | Asn | |
| | | | 100 | | | | | 105 | | | | | 110 | | | |
| tac | ctt | gga | gag | gct | gtg | agc | cac | aat | gca | tcg | ctg | gaa | gta | gcc | ata | 384 |
| Tyr | Leu | Gly | Glu | Ala | Val | Ser | His | Asn | Ala | Ser | Leu | Glu | Val | Ala | Ile | |
| | | 115 | | | | | 120 | | | | | 125 | | | | |
| ctt | cgg | gat | gac | ttc | aga | caa | aac | cct | tcg | gat | gtc | atg | gtt | gca | gta | 432 |
| Leu | Arg | Asp | Asp | Phe | Arg | Gln | Asn | Pro | Ser | Asp | Val | Met | Val | Ala | Val | |
| | 130 | | | | | 135 | | | | | 140 | | | | | |
| gga | gag | cct | gca | gta | atg | gaa | tgc | caa | cct | cca | cga | ggc | cat | cct | gag | 480 |
| Gly | Glu | Pro | Ala | Val | Met | Glu | Cys | Gln | Pro | Pro | Arg | Gly | His | Pro | Glu | |
| 145 | | | | | 150 | | | | | 155 | | | | | 160 | |
| ccc | acc | att | tca | tgg | aag | aaa | gat | ggc | tct | cca | ctg | gat | gat | aaa | gat | 528 |
| Pro | Thr | Ile | Ser | Trp | Lys | Lys | Asp | Gly | Ser | Pro | Leu | Asp | Asp | Lys | Asp | |
| | | | | 165 | | | | | 170 | | | | | 175 | | |
| gaa | aga | ata | act | ata | cga | gga | gga | aag | ctc | atg | atc | act | tac | acc | cgt | 576 |
| Glu | Arg | Ile | Thr | Ile | Arg | Gly | Gly | Lys | Leu | Met | Ile | Thr | Tyr | Thr | Arg | |
| | | | 180 | | | | | 185 | | | | | 190 | | | |
| aaa | agt | gac | gct | ggc | aaa | tat | gtt | tgt | gtt | ggt | acc | aat | atg | gtt | ggg | 624 |
| Lys | Ser | Asp | Ala | Gly | Lys | Tyr | Val | Cys | Val | Gly | Thr | Asn | Met | Val | Gly | |
| | | 195 | | | | | 200 | | | | | 205 | | | | |
| gaa | cgt | gag | agt | gaa | gta | gcc | gag | ctg | act | gtc | tta | gag | aga | cca | tca | 672 |
| Glu | Arg | Glu | Ser | Glu | Val | Ala | Glu | Leu | Thr | Val | Leu | Glu | Arg | Pro | Ser | |
| | 210 | | | | | 215 | | | | | 220 | | | | | |
| ttt | gtg | gag | tcc | aag | tac | ggc | cct | cct | tgc | cct | ccc | tgc | cct | gcc | cct | 720 |
| Phe | Val | Glu | Ser | Lys | Tyr | Gly | Pro | Pro | Cys | Pro | Pro | Cys | Pro | Ala | Pro | |
| 225 | | | | | 230 | | | | | 235 | | | | | 240 | |
| gag | ttc | gag | ggc | gga | cct | agc | gtg | ttc | ctg | ttc | cct | cct | aag | cct | aag | 768 |
| Glu | Phe | Glu | Gly | Gly | Pro | Ser | Val | Phe | Leu | Phe | Pro | Pro | Lys | Pro | Lys | |
| | | | | 245 | | | | | 250 | | | | | 255 | | |
| gac | acc | ctg | atg | atc | tcc | cgg | acc | cct | gag | gtg | acc | tgt | gtg | gtg | gtg | 816 |
| Asp | Thr | Leu | Met | Ile | Ser | Arg | Thr | Pro | Glu | Val | Thr | Cys | Val | Val | Val | |
| | | | 260 | | | | | 265 | | | | | 270 | | | |
| gac | gtg | tcc | cag | gag | gac | cct | gag | gtc | cag | ttc | aac | tgg | tac | gtg | gac | 864 |
| Asp | Val | Ser | Gln | Glu | Asp | Pro | Glu | Val | Gln | Phe | Asn | Trp | Tyr | Val | Asp | |
| | | 275 | | | | | 280 | | | | | 285 | | | | |
| ggc | gtg | gag | gtg | cac | aac | gcc | aag | acc | aag | cct | cgg | gag | gag | cag | ttc | 912 |

```
Gly Val Glu Val His Asn Ala Lys Thr Lys Pro Arg Glu Glu Gln Phe
        290                 295                 300 aat tcc acc tac cgg gtg gtg tct gtg ctg acc gtg ctg cac cag gac        960
Asn Ser Thr Tyr Arg Val Val Ser Val Leu Thr Val Leu His Gln Asp
305                 310                 315                 320 tgg ctg aac ggc aaa gaa tac aag tgt aag gtc tcc aac aag ggc ctg       1008
Trp Leu Asn Gly Lys Glu Tyr Lys Cys Lys Val Ser Asn Lys Gly Leu
                325                 330                 335 ccc tcc tcc atc gag aaa acc atc tcc aag gcc aag ggc cag cct agg       1056
Pro Ser Ser Ile Glu Lys Thr Ile Ser Lys Ala Lys Gly Gln Pro Arg
            340                 345                 350 gag cct cag gtg tac acc ctg cct cct agc cag gaa gag atg acc aag       1104
Glu Pro Gln Val Tyr Thr Leu Pro Pro Ser Gln Glu Glu Met Thr Lys
        355                 360                 365 aac cag gtg tcc ctg acc tgt ctg gtg aag ggc ttc tac cct tcc gac       1152
Asn Gln Val Ser Leu Thr Cys Leu Val Lys Gly Phe Tyr Pro Ser Asp
370                 375                 380 atc gcc gtg gag tgg gag tcc aac ggc cag cct gag aac aac tac aag       1200
Ile Ala Val Glu Trp Glu Ser Asn Gly Gln Pro Glu Asn Asn Tyr Lys
385                 390                 395                 400 acc acc cct cct gtg ctg gac tcc gac ggc tcc ttc ttc ctg tac tcc       1248
Thr Thr Pro Pro Val Leu Asp Ser Asp Gly Ser Phe Phe Leu Tyr Ser
                405                 410                 415 agg ctg acc gtg gac aag tcc cgg tgg cag gag ggc aac gtc ttt tcc       1296
Arg Leu Thr Val Asp Lys Ser Arg Trp Gln Glu Gly Asn Val Phe Ser
            420                 425                 430 tgc tcc gtg atg cac gag gcc ctg cac aac cac tac acc cag aag tcc       1344
Cys Ser Val Met His Glu Ala Leu His Asn His Tyr Thr Gln Lys Ser
        435                 440                 445 ctg tcc ctg tct ctg ggc tga                                           1365
Leu Ser Leu Ser Leu Gly
    450

<210> SEQ ID NO 10
<211> LENGTH: 454
<212> TYPE: PRT
<213> ORGANISM: Homo sapiens

<400> SEQUENCE: 10

Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Arg Ile Val
                20                  25                  30

Glu His Pro Ser Asp Leu Ile Val Ser Lys Gly Glu Pro Ala Thr Leu
            35                  40                  45

Asn Cys Lys Ala Glu Gly Arg Pro Thr Pro Thr Ile Glu Trp Tyr Lys
50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95

Ala Ala Ser Arg Pro Asp Glu Gly Val Tyr Val Cys Val Ala Arg Asn
            100                 105                 110

Tyr Leu Gly Glu Ala Val Ser His Asn Ala Ser Leu Glu Val Ala Ile
        115                 120                 125

Leu Arg Asp Asp Phe Arg Gln Asn Pro Ser Asp Val Met Val Ala Val
    130                 135                 140

Gly Glu Pro Ala Val Met Glu Cys Gln Pro Pro Arg Gly His Pro Glu
```

```
145                 150                 155                 160
Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
        195                 200                 205

Glu Arg Glu Ser Glu Val Ala Glu Leu Thr Val Leu Glu Arg Pro Ser
    210                 215                 220

Phe Val Glu Ser Lys Tyr Gly Pro Pro Cys Pro Pro Cys Pro Ala Pro
225                 230                 235                 240

Glu Phe Glu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly
    450

<210> SEQ ID NO 11
<211> LENGTH: 717
<212> TYPE: DNA
<213> ORGANISM: Homo sapiens
<220> FEATURE:
<221> NAME/KEY: CDS
<222> LOCATION: (1)..(717)

<400> SEQUENCE: 11 atg tac agg atg caa ctc ctg tct tgc att gca cta agt ctt gca ctt      48
Met Tyr Arg Met Gln Leu Leu Ser Cys Ile Ala Leu Ser Leu Ala Leu
1               5                   10                  15 gtc acg aat tca ttg cac tgc cct gcc gcc tgt acc tgt agc aac aat      96
Val Thr Asn Ser Leu His Cys Pro Ala Ala Cys Thr Cys Ser Asn Asn
            20                  25                  30 atc gta gac tgt cgt ggg aaa ggt ctc act gag atc ccc aca aat ctt     144
```

-continued

```
                Ile Val Asp Cys Arg Gly Lys Gly Leu Thr Glu Ile Pro Thr Asn Leu
                             35                  40                  45 cca gag acc atc aca gaa ata cgt ttg gaa cag aac aca atc aaa gtc            192
Pro Glu Thr Ile Thr Glu Ile Arg Leu Glu Gln Asn Thr Ile Lys Val
 50                  55                  60 atc cct cct gga gct ttc tca cca tat aaa aag ctt aga cga att gac            240
Ile Pro Pro Gly Ala Phe Ser Pro Tyr Lys Lys Leu Arg Arg Ile Asp
 65                  70                  75                  80 ctg agc aat aat cag atc tct gaa ctt gca cca gat gct ttc caa gga            288
Leu Ser Asn Asn Gln Ile Ser Glu Leu Ala Pro Asp Ala Phe Gln Gly
                     85                  90                  95 cta cgc tct ctg aat tca ctt gtc ctc tat gga aat aaa atc aca gaa            336
Leu Arg Ser Leu Asn Ser Leu Val Leu Tyr Gly Asn Lys Ile Thr Glu
                100                 105                 110 ctc ccc aaa agt tta ttt gaa gga ctg ttt tcc tta cag ctc cta tta            384
Leu Pro Lys Ser Leu Phe Glu Gly Leu Phe Ser Leu Gln Leu Leu Leu
                115                 120                 125 ttg aat gcc aac aag ata aac tgc ctt cgg gta gat gct ttt cag gat            432
Leu Asn Ala Asn Lys Ile Asn Cys Leu Arg Val Asp Ala Phe Gln Asp
130                 135                 140 ctc cac aac ttg aac ctt ctc tcc cta tat gac aac aag ctt cag acc            480
Leu His Asn Leu Asn Leu Leu Ser Leu Tyr Asp Asn Lys Leu Gln Thr
145                 150                 155                 160 atc gcc aag ggg acc ttt tca cct ctt cgg gcc att caa act atg cat            528
Ile Ala Lys Gly Thr Phe Ser Pro Leu Arg Ala Ile Gln Thr Met His
                165                 170                 175 ttg gcc cag aac ccc ttt att tgt gac tgc cat ctc aag tgg cta gcg            576
Leu Ala Gln Asn Pro Phe Ile Cys Asp Cys His Leu Lys Trp Leu Ala
                180                 185                 190 gat tat ctc cat acc aac ccg att gag acc agt ggt gcc cgt tgc acc            624
Asp Tyr Leu His Thr Asn Pro Ile Glu Thr Ser Gly Ala Arg Cys Thr
                195                 200                 205 agc ccc cgc cgc ctg gca aac aaa aga att gga cag atc aaa agc aag            672
Ser Pro Arg Arg Leu Ala Asn Lys Arg Ile Gly Gln Ile Lys Ser Lys
210                 215                 220 aaa ttc cgt tgt tca ggt agc gct cat cac cat cat cat cac tga                717
Lys Phe Arg Cys Ser Gly Ser Ala His His His His His His
225                 230                 235

<210> SEQ ID NO 12
<211> LENGTH: 238
<212> TYPE: PRT
<213> ORGANISM: Homo sapiens

<400> SEQUENCE: 12

Met Tyr Arg Met Gln Leu Leu Ser Cys Ile Ala Leu Ser Leu Ala Leu
 1               5                  10                  15

Val Thr Asn Ser Leu His Cys Pro Ala Ala Cys Thr Cys Ser Asn Asn
                20                  25                  30

Ile Val Asp Cys Arg Gly Lys Gly Leu Thr Glu Ile Pro Thr Asn Leu
             35                  40                  45

Pro Glu Thr Ile Thr Glu Ile Arg Leu Glu Gln Asn Thr Ile Lys Val
 50                  55                  60

Ile Pro Pro Gly Ala Phe Ser Pro Tyr Lys Lys Leu Arg Arg Ile Asp
 65                  70                  75                  80

Leu Ser Asn Asn Gln Ile Ser Glu Leu Ala Pro Asp Ala Phe Gln Gly
                     85                  90                  95

Leu Arg Ser Leu Asn Ser Leu Val Leu Tyr Gly Asn Lys Ile Thr Glu
                100                 105                 110
```

```
Leu Pro Lys Ser Leu Phe Glu Gly Leu Phe Ser Leu Gln Leu Leu
            115                 120                 125

Leu Asn Ala Asn Lys Ile Asn Cys Leu Arg Val Asp Ala Phe Gln Asp
        130                 135                 140

Leu His Asn Leu Asn Leu Leu Ser Leu Tyr Asp Asn Lys Leu Gln Thr
145                 150                 155                 160

Ile Ala Lys Gly Thr Phe Ser Pro Leu Arg Ala Ile Gln Thr Met His
                165                 170                 175

Leu Ala Gln Asn Pro Phe Ile Cys Asp Cys His Leu Lys Trp Leu Ala
            180                 185                 190

Asp Tyr Leu His Thr Asn Pro Ile Glu Thr Ser Gly Ala Arg Cys Thr
        195                 200                 205

Ser Pro Arg Arg Leu Ala Asn Lys Arg Ile Gly Gln Ile Lys Ser Lys
    210                 215                 220

Lys Phe Arg Cys Ser Gly Ser Ala His His His His His
225                 230                 235

<210> SEQ ID NO 13
<211> LENGTH: 1467
<212> TYPE: DNA
<213> ORGANISM: Homo sapiens
<220> FEATURE:
<221> NAME/KEY: CDS
<222> LOCATION: (1)..(1467)

<400> SEQUENCE: 13 atg cgc ggc gtt ggc tgg cag atg ctg tcc ctg tcg ctg ggg tta gtg      48
Met Arg Gly Val Gly Trp Gln Met Leu Ser Leu Ser Leu Gly Leu Val
1               5                   10                  15 ctg gcg atc ctg aac aag gtg gca ccg cag gcg tgc ccg gcg cag tgc      96
Leu Ala Ile Leu Asn Lys Val Ala Pro Gln Ala Cys Pro Ala Gln Cys
                20                  25                  30 tct tgc tcg ggc agc aca gtg gac tgt cac ggg ctg gcg ctg cgc agc     144
Ser Cys Ser Gly Ser Thr Val Asp Cys His Gly Leu Ala Leu Arg Ser
            35                  40                  45 gtg ccc agg aat atc ccc cgc aac acc gag aga ctg gat tta aat gga     192
Val Pro Arg Asn Ile Pro Arg Asn Thr Glu Arg Leu Asp Leu Asn Gly
        50                  55                  60 aat aac atc aca aga att acg aag aca gat ttt gct ggt ctt aga cat     240
Asn Asn Ile Thr Arg Ile Thr Lys Thr Asp Phe Ala Gly Leu Arg His
65                  70                  75                  80 cta aga gtt ctt cag ctt atg gag aat aag att agc acc att gaa aga     288
Leu Arg Val Leu Gln Leu Met Glu Asn Lys Ile Ser Thr Ile Glu Arg
                85                  90                  95 gga gca ttc cag gat ctt aaa gaa cta gag aga ctg cgt tta aac aga     336
Gly Ala Phe Gln Asp Leu Lys Glu Leu Glu Arg Leu Arg Leu Asn Arg
            100                 105                 110 aat cac ctt cag ctg ttt cct gag ttg ctg ttt ctt ggg act gcg aag     384
Asn His Leu Gln Leu Phe Pro Glu Leu Leu Phe Leu Gly Thr Ala Lys
        115                 120                 125 cta tac agg ctt gat ctc agt gaa aac caa att cag gca atc cca agg     432
Leu Tyr Arg Leu Asp Leu Ser Glu Asn Gln Ile Gln Ala Ile Pro Arg
    130                 135                 140 aaa gct ttc cgt ggg gca gtt gac ata aaa aat ttg caa ctg gat tac     480
Lys Ala Phe Arg Gly Ala Val Asp Ile Lys Asn Leu Gln Leu Asp Tyr
145                 150                 155                 160 aac cag atc agc tgt att gaa gat ggg gca ttc agg gct ctc cgg gac     528
Asn Gln Ile Ser Cys Ile Glu Asp Gly Ala Phe Arg Ala Leu Arg Asp
                165                 170                 175
```

```
ctg gaa gtg ctc act ctc aac aat aac aac att act aga ctt tct gtg        576
Leu Glu Val Leu Thr Leu Asn Asn Asn Asn Ile Thr Arg Leu Ser Val
            180                 185                 190 gca agt ttc aac cat atg cct aaa ctt agg act ttt cga ctg cat tca        624
Ala Ser Phe Asn His Met Pro Lys Leu Arg Thr Phe Arg Leu His Ser
        195                 200                 205 aac aac ctg tat tgt gac tgc cac ctg gcc tgg ctc tcc gac tgg ctt        672
Asn Asn Leu Tyr Cys Asp Cys His Leu Ala Trp Leu Ser Asp Trp Leu
        210                 215                 220 cgc caa agg cct cgg gtt ggt ctg tac act cag tgt atg ggc ccc tcc        720
Arg Gln Arg Pro Arg Val Gly Leu Tyr Thr Gln Cys Met Gly Pro Ser
225                 230                 235                 240 cac ctg aga ggc cat aat gta gcc gag gtt caa aaa cga gaa ttt gtc        768
His Leu Arg Gly His Asn Val Ala Glu Val Gln Lys Arg Glu Phe Val
            245                 250                 255 tgc agt ggt cac cag tca ttt atg gct cct tct tgt agt gtt ttg cac        816
Cys Ser Gly His Gln Ser Phe Met Ala Pro Ser Cys Ser Val Leu His
        260                 265                 270 tgc cct gcc gcc tgt acc tgt agc aac aat atc gta gac tgt cgt ggg        864
Cys Pro Ala Ala Cys Thr Cys Ser Asn Asn Ile Val Asp Cys Arg Gly
        275                 280                 285 aaa ggt ctc act gag atc ccc aca aat ctt cca gag acc atc aca gaa        912
Lys Gly Leu Thr Glu Ile Pro Thr Asn Leu Pro Glu Thr Ile Thr Glu
        290                 295                 300 ata cgt ttg gaa cag aac aca atc aaa gtc atc cct cct gga gct ttc        960
Ile Arg Leu Glu Gln Asn Thr Ile Lys Val Ile Pro Pro Gly Ala Phe
305                 310                 315                 320 tca cca tat aaa aag ctt aga cga att gac ctg agc aat aat cag atc       1008
Ser Pro Tyr Lys Lys Leu Arg Arg Ile Asp Leu Ser Asn Asn Gln Ile
            325                 330                 335 tct gaa ctt gca cca gat gct ttc caa gga cta cgc tct ctg aat tca       1056
Ser Glu Leu Ala Pro Asp Ala Phe Gln Gly Leu Arg Ser Leu Asn Ser
        340                 345                 350 ctt gtc ctc tat gga aat aaa atc aca gaa ctc ccc aaa agt tta ttt       1104
Leu Val Leu Tyr Gly Asn Lys Ile Thr Glu Leu Pro Lys Ser Leu Phe
        355                 360                 365 gaa gga ctg ttt tcc tta cag ctc cta tta ttg aat gcc aac aag ata       1152
Glu Gly Leu Phe Ser Leu Gln Leu Leu Leu Leu Asn Ala Asn Lys Ile
370                 375                 380 aac tgc ctt cgg gta gat gct ttt cag gat ctc cac aac ttg aac ctt       1200
Asn Cys Leu Arg Val Asp Ala Phe Gln Asp Leu His Asn Leu Asn Leu
385                 390                 395                 400 ctc tcc cta tat gac aac aag ctt cag acc atc gcc aag ggg acc ttt       1248
Leu Ser Leu Tyr Asp Asn Lys Leu Gln Thr Ile Ala Lys Gly Thr Phe
            405                 410                 415 tca cct ctt cgg gcc att caa act atg cat ttg gcc cag aac ccc ttt       1296
Ser Pro Leu Arg Ala Ile Gln Thr Met His Leu Ala Gln Asn Pro Phe
        420                 425                 430 att tgt gac tgc cat ctc aag tgg cta gcg gat tat ctc cat acc aac       1344
Ile Cys Asp Cys His Leu Lys Trp Leu Ala Asp Tyr Leu His Thr Asn
        435                 440                 445 ccg att gag acc agt ggt gcc cgt tgc acc agc ccc gcc cgc ctg gca       1392
Pro Ile Glu Thr Ser Gly Ala Arg Cys Thr Ser Pro Arg Arg Leu Ala
450                 455                 460 aac aaa aga att gga cag atc aaa agc aag aaa ttc gtt tgt tca ggt       1440
Asn Lys Arg Ile Gly Gln Ile Lys Ser Lys Lys Phe Arg Cys Ser Gly
465                 470                 475                 480 agc gct cat cac cat cat cat cac tga                                   1467
Ser Ala His His His His His His
```

-continued

485

<210> SEQ ID NO 14
<211> LENGTH: 488
<212> TYPE: PRT
<213> ORGANISM: Homo sapiens

<400> SEQUENCE: 14

Met Arg Gly Val Gly Trp Gln Met Leu Ser Leu Ser Leu Gly Leu Val
1               5                   10                  15

Leu Ala Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Gly His Gln Ser Phe Met Ala Pro Ser Cys Ser Val Leu His
            260                 265                 270

Cys Pro Ala Ala Cys Thr Cys Ser Asn Asn Ile Val Asp Cys Arg Gly
        275                 280                 285

Lys Gly Leu Thr Glu Ile Pro Thr Asn Leu Pro Glu Thr Ile Thr Glu
    290                 295                 300

Ile Arg Leu Glu Gln Asn Thr Ile Lys Val Ile Pro Pro Gly Ala Phe
305                 310                 315                 320

Ser Pro Tyr Lys Lys Leu Arg Arg Ile Asp Leu Ser Asn Asn Gln Ile
                325                 330                 335

Ser Glu Leu Ala Pro Asp Ala Phe Gln Gly Leu Arg Ser Leu Asn Ser
            340                 345                 350

Leu Val Leu Tyr Gly Asn Lys Ile Thr Glu Leu Pro Lys Ser Leu Phe
        355                 360                 365

```
Glu Gly Leu Phe Ser Leu Gln Leu Leu Leu Asn Ala Asn Lys Ile
    370                 375                 380
Asn Cys Leu Arg Val Asp Ala Phe Gln Asp Leu His Asn Leu Asn Leu
385                 390                 395                 400
Leu Ser Leu Tyr Asp Asn Lys Leu Gln Thr Ile Ala Lys Gly Thr Phe
                405                 410                 415
Ser Pro Leu Arg Ala Ile Gln Thr Met His Leu Ala Gln Asn Pro Phe
            420                 425                 430
Ile Cys Asp Cys His Leu Lys Trp Leu Ala Asp Tyr Leu His Thr Asn
                435                 440                 445
Pro Ile Glu Thr Ser Gly Ala Arg Cys Thr Ser Pro Arg Arg Leu Ala
    450                 455                 460
Asn Lys Arg Ile Gly Gln Ile Lys Ser Lys Phe Arg Cys Ser Gly
465                 470                 475                 480
Ser Ala His His His His His His
            485
```

<210> SEQ ID NO 15
<211> LENGTH: 3390
<212> TYPE: DNA
<213> ORGANISM: Homo sapiens
<220> FEATURE:
<221> NAME/KEY: CDS
<222> LOCATION: (1)..(3390)

<400> SEQUENCE: 15

```
atg cgc ggc gtt ggc tgg cag atg ctg tcc ctg tcg ctg ggg tta gtg      48
Met Arg Gly Val Gly Trp Gln Met Leu Ser Leu Ser Leu Gly Leu Val
1               5                   10                  15 ctg gcg atc ctg aac aag gtg gca ccg cag gcg tgc ccg gcg cag tgc      96
Leu Ala Ile Leu Asn Lys Val Ala Pro Gln Ala Cys Pro Ala Gln Cys
                20                  25                  30 tct tgc tcg ggc agc aca gtg gac tgt cac ggg ctg gcg ctg cgc agc     144
Ser Cys Ser Gly Ser Thr Val Asp Cys His Gly Leu Ala Leu Arg Ser
            35                  40                  45 gtg ccc agg aat atc ccc cgc aac acc gag aga ctg gat tta aat gga     192
Val Pro Arg Asn Ile Pro Arg Asn Thr Glu Arg Leu Asp Leu Asn Gly
        50                  55                  60 aat aac atc aca aga att acg aag aca gat ttt gct ggt ctt aga cat     240
Asn Asn Ile Thr Arg Ile Thr Lys Thr Asp Phe Ala Gly Leu Arg His
65                  70                  75                  80 cta aga gtt ctt cag ctt atg gag aat aag att agc acc att gaa aga     288
Leu Arg Val Leu Gln Leu Met Glu Asn Lys Ile Ser Thr Ile Glu Arg
                85                  90                  95 gga gca ttc cag gat ctt aaa gaa cta gag aga ctg cgt tta aac aga     336
Gly Ala Phe Gln Asp Leu Lys Glu Leu Glu Arg Leu Arg Leu Asn Arg
            100                 105                 110 aat cac ctt cag ctg ttt cct gag ttg ctg ttt ctt ggg act gcg aag     384
Asn His Leu Gln Leu Phe Pro Glu Leu Leu Phe Leu Gly Thr Ala Lys
        115                 120                 125 cta tac agg ctt gat ctc agt gaa aac caa att cag gca atc cca agg     432
Leu Tyr Arg Leu Asp Leu Ser Glu Asn Gln Ile Gln Ala Ile Pro Arg
    130                 135                 140 aaa gct ttc cgt ggg gca gtt gac ata aaa aat ttg caa ctg gat tac     480
Lys Ala Phe Arg Gly Ala Val Asp Ile Lys Asn Leu Gln Leu Asp Tyr
145                 150                 155                 160 aac cag atc agc tgt att gaa gat ggg gca ttc agg gct ctc cgg gac     528
Asn Gln Ile Ser Cys Ile Glu Asp Gly Ala Phe Arg Ala Leu Arg Asp
                165                 170                 175
```

-continued

| | |
|---|---|
| ctg gaa gtg ctc act ctc aac aat aac aac att act aga ctt tct gtg<br>Leu Glu Val Leu Thr Leu Asn Asn Asn Asn Ile Thr Arg Leu Ser Val<br>180                         185                   190 | 576 |
| gca agt ttc aac cat atg cct aaa ctt agg act ttt cga ctg cat tca<br>Ala Ser Phe Asn His Met Pro Lys Leu Arg Thr Phe Arg Leu His Ser<br>195                    200                   205 | 624 |
| aac aac ctg tat tgt gac tgc cac ctg gcc tgg ctc tcc gac tgg ctt<br>Asn Asn Leu Tyr Cys Asp Cys His Leu Ala Trp Leu Ser Asp Trp Leu<br>210                       215                   220 | 672 |
| cgc caa agg cct cgg gtt ggt ctg tac act cag tgt atg ggc ccc tcc<br>Arg Gln Arg Pro Arg Val Gly Leu Tyr Thr Gln Cys Met Gly Pro Ser<br>225                       230                 235               240 | 720 |
| cac ctg aga ggc cat aat gta gcc gag gtt caa aaa cga gaa ttt gtc<br>His Leu Arg Gly His Asn Val Ala Glu Val Gln Lys Arg Glu Phe Val<br>                          245                   250               255 | 768 |
| tgc agt ggt cac cag tca ttt atg gct cct tct tgt agt gtt ttg cac<br>Cys Ser Gly His Gln Ser Phe Met Ala Pro Ser Cys Ser Val Leu His<br>          260                   265                   270 | 816 |
| tgc cct gcc gcc tgt acc tgt agc aac aat atc gta gac tgt cgt ggg<br>Cys Pro Ala Ala Cys Thr Cys Ser Asn Asn Ile Val Asp Cys Arg Gly<br>275                       280                   285 | 864 |
| aaa ggt ctc act gag atc ccc aca aat ctt cca gag acc atc aca gaa<br>Lys Gly Leu Thr Glu Ile Pro Thr Asn Leu Pro Glu Thr Ile Thr Glu<br>290                       295                   300 | 912 |
| ata cgt ttg gaa cag aac aca atc aaa gtc atc cct cct gga gct ttc<br>Ile Arg Leu Glu Gln Asn Thr Ile Lys Val Ile Pro Pro Gly Ala Phe<br>305                       310                   315               320 | 960 |
| tca cca tat aaa aag ctt aga cga att gac ctg agc aat aat cag atc<br>Ser Pro Tyr Lys Lys Leu Arg Arg Ile Asp Leu Ser Asn Asn Gln Ile<br>                          325                   330               335 | 1008 |
| tct gaa ctt gca cca gat gct ttc caa gga cta cgc tct ctg aat tca<br>Ser Glu Leu Ala Pro Asp Ala Phe Gln Gly Leu Arg Ser Leu Asn Ser<br>                    340                   345               350 | 1056 |
| ctt gtc ctc tat gga aat aaa atc aca gaa ctc ccc aaa agt tta ttt<br>Leu Val Leu Tyr Gly Asn Lys Ile Thr Glu Leu Pro Lys Ser Leu Phe<br>                         355                   360               365 | 1104 |
| gaa gga ctg ttt tcc tta cag ctc cta tta ttg aat gcc aac aag ata<br>Glu Gly Leu Phe Ser Leu Gln Leu Leu Leu Leu Asn Ala Asn Lys Ile<br>370                       375                   380 | 1152 |
| aac tgc ctt cgg gta gat gct ttt cag gat ctc cac aac ttg aac ctt<br>Asn Cys Leu Arg Val Asp Ala Phe Gln Asp Leu His Asn Leu Asn Leu<br>385                       390                   395               400 | 1200 |
| ctc tcc cta tat gac aac aag ctt cag acc atc gcc aag ggg acc ttt<br>Leu Ser Leu Tyr Asp Asn Lys Leu Gln Thr Ile Ala Lys Gly Thr Phe<br>                         405                   410               415 | 1248 |
| tca cct ctt cgg gcc att caa act atg cat ttg gcc cag aac ccc ttt<br>Ser Pro Leu Arg Ala Ile Gln Thr Met His Leu Ala Gln Asn Pro Phe<br>420                       425                   430 | 1296 |
| att tgt gac tgc cat ctc aag tgg cta gcg gat tat ctc cat acc aac<br>Ile Cys Asp Cys His Leu Lys Trp Leu Ala Asp Tyr Leu His Thr Asn<br>                    435                   440               445 | 1344 |
| ccg att gag acc agt ggt gcc cgt tgc acc agc ccc cgc cgc ctg gca<br>Pro Ile Glu Thr Ser Gly Ala Arg Cys Thr Ser Pro Arg Arg Leu Ala<br>450                       455                   460 | 1392 |
| aac aaa aga att gga cag atc aaa agc aag aaa ttc cgt tgt tca gct<br>Asn Lys Arg Ile Gly Gln Ile Lys Ser Lys Lys Phe Arg Cys Ser Ala<br>465                       470                   475               480 | 1440 |
| aaa gaa cag tat ttc att cca ggt aca gaa gat tat cga tca aaa tta<br>Lys Glu Gln Tyr Phe Ile Pro Gly Thr Glu Asp Tyr Arg Ser Lys Leu<br>                         485                   490               495 | 1488 |

-continued

| | |
|---|---|
| agt gga gac tgc ttt gcg gat ctg gct tgc cct gaa aag tgt cgc tgt<br>Ser Gly Asp Cys Phe Ala Asp Leu Ala Cys Pro Glu Lys Cys Arg Cys<br>          500                  505                510 | 1536 |
| gaa gga acc aca gta gat tgc tct aat caa aag ctc aac aaa atc ccg<br>Glu Gly Thr Thr Val Asp Cys Ser Asn Gln Lys Leu Asn Lys Ile Pro<br>          515                  520                525 | 1584 |
| gag cac att ccc cag tac act gca gag ttg cgt ctc aat aat aat gaa<br>Glu His Ile Pro Gln Tyr Thr Ala Glu Leu Arg Leu Asn Asn Asn Glu<br>530                  535                    540 | 1632 |
| ttt acc gtg ttg gaa gcc aca gga atc ttt aag aaa ctt cct caa tta<br>Phe Thr Val Leu Glu Ala Thr Gly Ile Phe Lys Lys Leu Pro Gln Leu<br>545                  550                555                560 | 1680 |
| cgt aaa ata aac ttt agc aac aat aag atc aca gat att gag gag gga<br>Arg Lys Ile Asn Phe Ser Asn Asn Lys Ile Thr Asp Ile Glu Glu Gly<br>                  565                  570                575 | 1728 |
| gca ttt gaa gga gca tct ggt gta aat gaa ata ctt ctt acg agt aat<br>Ala Phe Glu Gly Ala Ser Gly Val Asn Glu Ile Leu Leu Thr Ser Asn<br>                    580                  585                590 | 1776 |
| cgt ttg gaa aat gtg cag cat aag atg ttc aag gga ttg gaa agc ctc<br>Arg Leu Glu Asn Val Gln His Lys Met Phe Lys Gly Leu Glu Ser Leu<br>          595                  600                605 | 1824 |
| aaa act ttg atg ttg aga agc aat cga ata acc tgt gtg ggg aat gac<br>Lys Thr Leu Met Leu Arg Ser Asn Arg Ile Thr Cys Val Gly Asn Asp<br>610                  615                    620 | 1872 |
| agt ttc ata gga ctc agt tct gtg cgt ttg ctt tct ttg tat gat aat<br>Ser Phe Ile Gly Leu Ser Ser Val Arg Leu Leu Ser Leu Tyr Asp Asn<br>625                  630                635                640 | 1920 |
| caa att act aca gtt gca cca ggg gca ttt gat act ctc cat tct tta<br>Gln Ile Thr Thr Val Ala Pro Gly Ala Phe Asp Thr Leu His Ser Leu<br>                    645                  650                655 | 1968 |
| tct act cta aac ctc ttg gcc aat cct ttt aac tgt aac tgc tac ctg<br>Ser Thr Leu Asn Leu Leu Ala Asn Pro Phe Asn Cys Asn Cys Tyr Leu<br>                    660                  665                670 | 2016 |
| gct tgg ttg gga gag tgg ctg aga aag aag aga att gtc acg gga aat<br>Ala Trp Leu Gly Glu Trp Leu Arg Lys Lys Arg Ile Val Thr Gly Asn<br>          675                  680                685 | 2064 |
| cct aga tgt caa aaa cca tac ttc ctg aaa gaa ata ccc atc cag gat<br>Pro Arg Cys Gln Lys Pro Tyr Phe Leu Lys Glu Ile Pro Ile Gln Asp<br>690                  695                    700 | 2112 |
| gtg gcc att cag gac ttc act tgt gat gac gga aat gat gac aat agt<br>Val Ala Ile Gln Asp Phe Thr Cys Asp Asp Gly Asn Asp Asp Asn Ser<br>705                  710                715                720 | 2160 |
| tgc tcc cca ctt tct cgc tgt cct act gaa tgt act tgc ttg gat aca<br>Cys Ser Pro Leu Ser Arg Cys Pro Thr Glu Cys Thr Cys Leu Asp Thr<br>                    725                  730                735 | 2208 |
| gtc gtc cga tgt agc aac aag ggt ttg aag gtc ttg ccg aaa ggt att<br>Val Val Arg Cys Ser Asn Lys Gly Leu Lys Val Leu Pro Lys Gly Ile<br>                  740                  745                750 | 2256 |
| cca aga gat gtc aca gag ttg tat ctg gat gga aac caa ttt aca ctg<br>Pro Arg Asp Val Thr Glu Leu Tyr Leu Asp Gly Asn Gln Phe Thr Leu<br>          755                  760                765 | 2304 |
| gtt ccc aag gaa ctc tcc aac tac aaa cat tta aca ctt ata gac tta<br>Val Pro Lys Glu Leu Ser Asn Tyr Lys His Leu Thr Leu Ile Asp Leu<br>770                  775                780 | 2352 |
| agt aac aac aga ata agc acg ctt tct aat cag agc ttc agc aac atg<br>Ser Asn Asn Arg Ile Ser Thr Leu Ser Asn Gln Ser Phe Ser Asn Met<br>785                  790                795                800 | 2400 |
| acc cag ctc ctc acc tta att ctt agt tac aac cgt ctg aga tgt att<br>Thr Gln Leu Leu Thr Leu Ile Leu Ser Tyr Asn Arg Leu Arg Cys Ile | 2448 |

-continued

```
                805                 810                 815
cct cct cgc acc ttt gat gga tta aag tct ctt cga tta ctt tct cta    2496
Pro Pro Arg Thr Phe Asp Gly Leu Lys Ser Leu Arg Leu Leu Ser Leu
            820                 825                 830 cat gga aat gac att tct gtt gtg cct gaa ggt gct ttc aat gat ctt    2544
His Gly Asn Asp Ile Ser Val Val Pro Glu Gly Ala Phe Asn Asp Leu
            835                 840                 845 tct gca tta tca cat cta gca att gga gcc aac cct ctt tac tgt gat    2592
Ser Ala Leu Ser His Leu Ala Ile Gly Ala Asn Pro Leu Tyr Cys Asp
    850                 855                 860 tgt aac atg cag tgg tta tcc gac tgg gtg aag tcg gaa tat aag gag    2640
Cys Asn Met Gln Trp Leu Ser Asp Trp Val Lys Ser Glu Tyr Lys Glu
865                 870                 875                 880 cct gga att gct cgt tgt gct ggt cct gga gaa atg gca gat aaa ctt    2688
Pro Gly Ile Ala Arg Cys Ala Gly Pro Gly Glu Met Ala Asp Lys Leu
                885                 890                 895 tta ctc aca act ccc tcc aaa aaa ttt acc tgt caa ggt cct gtg gat    2736
Leu Leu Thr Thr Pro Ser Lys Lys Phe Thr Cys Gln Gly Pro Val Asp
            900                 905                 910 gtc aat att cta gct aag tgt aac ccc tgc cta tca aat ccg tgt aaa    2784
Val Asn Ile Leu Ala Lys Cys Asn Pro Cys Leu Ser Asn Pro Cys Lys
            915                 920                 925 aat gat ggc aca tgt aat agt gat cca gtt gac ttt tac cga tgc acc    2832
Asn Asp Gly Thr Cys Asn Ser Asp Pro Val Asp Phe Tyr Arg Cys Thr
    930                 935                 940 tgt cca tat ggt ttc aag ggg cag gac tgt gat gtc cca att cat gcc    2880
Cys Pro Tyr Gly Phe Lys Gly Gln Asp Cys Asp Val Pro Ile His Ala
945                 950                 955                 960 tgc atc agt aac cca tgt aaa cat gga gga act tgc cac tta aag gaa    2928
Cys Ile Ser Asn Pro Cys Lys His Gly Gly Thr Cys His Leu Lys Glu
                965                 970                 975 gga gaa gaa gat gga ttc tgg tgt att tgt gct gat gga ttt gaa gga    2976
Gly Glu Glu Asp Gly Phe Trp Cys Ile Cys Ala Asp Gly Phe Glu Gly
            980                 985                 990 gaa aat tgt gaa gtc aac gtt gat  gat tgt gaa gat aat  gac tgt gaa    3024
Glu Asn Cys Glu Val Asn Val Asp Asp Cys Glu Asp Asn Asp Cys Glu
            995                 1000                1005 aat aat tct aca tgt gtc gat  ggc att aat aac tac aca tgc ctt        3069
Asn Asn Ser Thr Cys Val Asp Gly Ile Asn Asn Tyr Thr Cys Leu
    1010                1015                1020 tgc cca cct gag tat aca ggt gag ttg tgt gag gag aag ctg gac        3114
Cys Pro Pro Glu Tyr Thr Gly Glu Leu Cys Glu Glu Lys Leu Asp
    1025                1030                1035 ttc tgt gcc cag gac ctg aac ccc tgc cag cac gat tca aag tgc        3159
Phe Cys Ala Gln Asp Leu Asn Pro Cys Gln His Asp Ser Lys Cys
    1040                1045                1050 atc cta act cca aag gga ttc aaa tgt gac tgc aca cca ggg tac        3204
Ile Leu Thr Pro Lys Gly Phe Lys Cys Asp Cys Thr Pro Gly Tyr
    1055                1060                1065 gta ggt gaa cac tgc gac atc gat ttt gac gac tgc caa gac aac        3249
Val Gly Glu His Cys Asp Ile Asp Phe Asp Asp Cys Gln Asp Asn
    1070                1075                1080 aag tgt aaa aac gga gcc cac tgc aca gat gca gtg aac ggc tat        3294
Lys Cys Lys Asn Gly Ala His Cys Thr Asp Ala Val Asn Gly Tyr
    1085                1090                1095 acg tgc ata tgc ccc gaa ggt tac agt ggc ttg ttc tgt gag ttt        3339
Thr Cys Ile Cys Pro Glu Gly Tyr Ser Gly Leu Phe Cys Glu Phe
    1100                1105                1110 tct cca ccc atg gtc ctc cct cgt agc gct cat cac cat cat cat        3384
```

```
Ser Pro Pro Met Val Leu Pro Arg Ser Ala His His His His His
    1115                1120                    1125 cac tga                                                              3390
His
```

<210> SEQ ID NO 16
<211> LENGTH: 1129
<212> TYPE: PRT
<213> ORGANISM: Homo sapiens

<400> SEQUENCE: 16

```
Met Arg Gly Val Gly Trp Gln Met Leu Ser Leu Ser Leu Gly Leu Val
1               5                   10                  15

Leu Ala Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Gly His Gln Ser Phe Met Ala Pro Ser Cys Ser Val Leu His
            260                 265                 270

Cys Pro Ala Ala Cys Thr Cys Ser Asn Asn Ile Val Asp Cys Arg Gly
        275                 280                 285

Lys Gly Leu Thr Glu Ile Pro Thr Asn Leu Pro Glu Thr Ile Thr Glu
290                 295                 300

Ile Arg Leu Glu Gln Asn Thr Ile Lys Val Ile Pro Pro Gly Ala Phe
305                 310                 315                 320

Ser Pro Tyr Lys Lys Leu Arg Arg Ile Asp Leu Ser Asn Asn Gln Ile
                325                 330                 335

Ser Glu Leu Ala Pro Asp Ala Phe Gln Gly Leu Arg Ser Leu Asn Ser
            340                 345                 350
```

```
Leu Val Leu Tyr Gly Asn Lys Ile Thr Glu Leu Pro Lys Ser Leu Phe
            355                 360                 365

Glu Gly Leu Phe Ser Leu Gln Leu Leu Leu Asn Ala Asn Lys Ile
370                 375                 380

Asn Cys Leu Arg Val Asp Ala Phe Gln Asp Leu His Asn Leu Asn Leu
385                 390                 395                 400

Leu Ser Leu Tyr Asp Asn Lys Leu Gln Thr Ile Ala Lys Gly Thr Phe
                405                 410                 415

Ser Pro Leu Arg Ala Ile Gln Thr Met His Leu Ala Gln Asn Pro Phe
                420                 425                 430

Ile Cys Asp Cys His Leu Lys Trp Leu Ala Asp Tyr Leu His Thr Asn
                435                 440                 445

Pro Ile Glu Thr Ser Gly Ala Arg Cys Thr Ser Pro Arg Arg Leu Ala
                450                 455                 460

Asn Lys Arg Ile Gly Gln Ile Lys Ser Lys Lys Phe Arg Cys Ser Ala
465                 470                 475                 480

Lys Glu Gln Tyr Phe Ile Pro Gly Thr Glu Asp Tyr Arg Ser Lys Leu
                485                 490                 495

Ser Gly Asp Cys Phe Ala Asp Leu Ala Cys Pro Glu Lys Cys Arg Cys
                500                 505                 510

Glu Gly Thr Thr Val Asp Cys Ser Asn Gln Lys Leu Asn Lys Ile Pro
                515                 520                 525

Glu His Ile Pro Gln Tyr Thr Ala Glu Leu Arg Leu Asn Asn Asn Glu
                530                 535                 540

Phe Thr Val Leu Glu Ala Thr Gly Ile Phe Lys Lys Leu Pro Gln Leu
545                 550                 555                 560

Arg Lys Ile Asn Phe Ser Asn Asn Lys Ile Thr Asp Ile Glu Glu Gly
                565                 570                 575

Ala Phe Glu Gly Ala Ser Gly Val Asn Glu Ile Leu Leu Thr Ser Asn
                580                 585                 590

Arg Leu Glu Asn Val Gln His Lys Met Phe Lys Gly Leu Glu Ser Leu
                595                 600                 605

Lys Thr Leu Met Leu Arg Ser Asn Arg Ile Thr Cys Val Gly Asn Asp
                610                 615                 620

Ser Phe Ile Gly Leu Ser Ser Val Arg Leu Leu Ser Leu Tyr Asp Asn
625                 630                 635                 640

Gln Ile Thr Thr Val Ala Pro Gly Ala Phe Asp Thr Leu His Ser Leu
                645                 650                 655

Ser Thr Leu Asn Leu Leu Ala Asn Pro Phe Asn Cys Asn Cys Tyr Leu
                660                 665                 670

Ala Trp Leu Gly Glu Trp Leu Arg Lys Lys Arg Ile Val Thr Gly Asn
                675                 680                 685

Pro Arg Cys Gln Lys Pro Tyr Phe Leu Lys Glu Ile Pro Ile Gln Asp
                690                 695                 700

Val Ala Ile Gln Asp Phe Thr Cys Asp Asp Gly Asn Asp Asn Ser
705                 710                 715                 720

Cys Ser Pro Leu Ser Arg Cys Pro Thr Glu Cys Thr Cys Leu Asp Thr
                725                 730                 735

Val Val Arg Cys Ser Asn Lys Gly Leu Lys Val Leu Pro Lys Gly Ile
                740                 745                 750

Pro Arg Asp Val Thr Glu Leu Tyr Leu Asp Gly Asn Gln Phe Thr Leu
                755                 760                 765
```

```
Val Pro Lys Glu Leu Ser Asn Tyr Lys His Leu Thr Leu Ile Asp Leu
    770                 775                 780
Ser Asn Asn Arg Ile Ser Thr Leu Ser Asn Gln Ser Phe Ser Asn Met
785                 790                 795                 800
Thr Gln Leu Leu Thr Leu Ile Leu Ser Tyr Asn Arg Leu Arg Cys Ile
                805                 810                 815
Pro Pro Arg Thr Phe Asp Gly Leu Lys Ser Leu Arg Leu Leu Ser Leu
            820                 825                 830
His Gly Asn Asp Ile Ser Val Val Pro Glu Gly Ala Phe Asn Asp Leu
        835                 840                 845
Ser Ala Leu Ser His Leu Ala Ile Gly Ala Asn Pro Leu Tyr Cys Asp
850                 855                 860
Cys Asn Met Gln Trp Leu Ser Asp Trp Val Lys Ser Glu Tyr Lys Glu
865                 870                 875                 880
Pro Gly Ile Ala Arg Cys Ala Gly Pro Gly Glu Met Ala Asp Lys Leu
                885                 890                 895
Leu Leu Thr Thr Pro Ser Lys Lys Phe Thr Cys Gln Gly Pro Val Asp
            900                 905                 910
Val Asn Ile Leu Ala Lys Cys Asn Pro Cys Leu Ser Asn Pro Cys Lys
        915                 920                 925
Asn Asp Gly Thr Cys Asn Ser Asp Pro Val Asp Phe Tyr Arg Cys Thr
930                 935                 940
Cys Pro Tyr Gly Phe Lys Gly Gln Asp Cys Asp Val Pro Ile His Ala
945                 950                 955                 960
Cys Ile Ser Asn Pro Cys Lys His Gly Gly Thr Cys His Leu Lys Glu
                965                 970                 975
Gly Glu Glu Asp Gly Phe Trp Cys Ile Cys Ala Asp Gly Phe Glu Gly
            980                 985                 990
Glu Asn Cys Glu Val Asn Val Asp Asp Cys Glu Asp Asn Asp Cys Glu
        995                 1000                1005
Asn Asn Ser Thr Cys Val Asp Gly Ile Asn Asn Tyr Thr Cys Leu
    1010                1015                1020
Cys Pro Pro Glu Tyr Thr Gly Glu Leu Cys Glu Glu Lys Leu Asp
    1025                1030                1035
Phe Cys Ala Gln Asp Leu Asn Pro Cys Gln His Asp Ser Lys Cys
    1040                1045                1050
Ile Leu Thr Pro Lys Gly Phe Lys Cys Asp Cys Thr Pro Gly Tyr
    1055                1060                1065
Val Gly Glu His Cys Asp Ile Asp Phe Asp Asp Cys Gln Asp Asn
    1070                1075                1080
Lys Cys Lys Asn Gly Ala His Cys Thr Asp Ala Val Asn Gly Tyr
    1085                1090                1095
Thr Cys Ile Cys Pro Glu Gly Tyr Ser Gly Leu Phe Cys Glu Phe
    1100                1105                1110
Ser Pro Pro Met Val Leu Pro Arg Ser Ala His His His His His
    1115                1120                1125
His
```

<210> SEQ ID NO 17
<211> LENGTH: 717
<212> TYPE: DNA
<213> ORGANISM: Mus musculus
<220> FEATURE:
<221> NAME/KEY: CDS
<222> LOCATION: (1)..(717)

```
<400> SEQUENCE: 17 atg tac agg atg caa ctc ctg tct tgc att gca cta agt ctt gca ctt        48
Met Tyr Arg Met Gln Leu Leu Ser Cys Ile Ala Leu Ser Leu Ala Leu
1               5                   10                  15 gtc acg aat tca ttg cac tgc cct gcc gcc tgt acc tgt agc aac aat        96
Val Thr Asn Ser Leu His Cys Pro Ala Ala Cys Thr Cys Ser Asn Asn
            20                  25                  30 atc gta gac tgt cgt ggg aaa ggt ctc act gag atc ccc aca aat ctt       144
Ile Val Asp Cys Arg Gly Lys Gly Leu Thr Glu Ile Pro Thr Asn Leu
        35                  40                  45 cca gag acc atc aca gaa ata cgt ttg gaa cag aac agc atc aga gtc       192
Pro Glu Thr Ile Thr Glu Ile Arg Leu Glu Gln Asn Ser Ile Arg Val
    50                  55                  60 atc cct cct gga gct ttc tca cca tat aaa aag ctt aga cga ctg gac       240
Ile Pro Pro Gly Ala Phe Ser Pro Tyr Lys Lys Leu Arg Arg Leu Asp
65                  70                  75                  80 ctg agc aat aat cag atc tct gaa ctt gca cca gat gct ttc caa gga       288
Leu Ser Asn Asn Gln Ile Ser Glu Leu Ala Pro Asp Ala Phe Gln Gly
                85                  90                  95 cta cgc tct ctg aat tca ctt gtc ctc tat gga aat aaa atc aca gaa       336
Leu Arg Ser Leu Asn Ser Leu Val Leu Tyr Gly Asn Lys Ile Thr Glu
            100                 105                 110 ctc ccc aaa agt tta ttt gaa gga ctg ttt tcc tta cag ctc cta tta       384
Leu Pro Lys Ser Leu Phe Glu Gly Leu Phe Ser Leu Gln Leu Leu Leu
        115                 120                 125 ttg aat gcc aac aag ata aac tgc ctt cgg gta gat gct ttt cag gat       432
Leu Asn Ala Asn Lys Ile Asn Cys Leu Arg Val Asp Ala Phe Gln Asp
    130                 135                 140 ctc cac aac ttg aac ctt ctc tcc cta tat gac aac aag ctt cag acc       480
Leu His Asn Leu Asn Leu Leu Ser Leu Tyr Asp Asn Lys Leu Gln Thr
145                 150                 155                 160 gtc gcc aag ggg acc ttt tca gct ctt cgg gcc att caa act atg cat       528
Val Ala Lys Gly Thr Phe Ser Ala Leu Arg Ala Ile Gln Thr Met His
                165                 170                 175 ttg gcc cag aac ccc ttt att tgt gac tgc cat ctc aag tgg cta gcg       576
Leu Ala Gln Asn Pro Phe Ile Cys Asp Cys His Leu Lys Trp Leu Ala
            180                 185                 190 gat tat ctc cat acc aac ccg att gag acc agt ggt gcc cgt tgc acc       624
Asp Tyr Leu His Thr Asn Pro Ile Glu Thr Ser Gly Ala Arg Cys Thr
        195                 200                 205 agc ccc cgc cgc ctg gca aac aaa aga att gga cag atc aaa agc aag       672
Ser Pro Arg Arg Leu Ala Asn Lys Arg Ile Gly Gln Ile Lys Ser Lys
    210                 215                 220 aaa ttc cgt tgt tca ggt agc gct cat cac cat cat cat cac tga           717
Lys Phe Arg Cys Ser Gly Ser Ala His His His His His His
225                 230                 235

<210> SEQ ID NO 18
<211> LENGTH: 238
<212> TYPE: PRT
<213> ORGANISM: Mus musculus

<400> SEQUENCE: 18

Met Tyr Arg Met Gln Leu Leu Ser Cys Ile Ala Leu Ser Leu Ala Leu
1               5                   10                  15

Val Thr Asn Ser Leu His Cys Pro Ala Ala Cys Thr Cys Ser Asn Asn
            20                  25                  30

Ile Val Asp Cys Arg Gly Lys Gly Leu Thr Glu Ile Pro Thr Asn Leu
        35                  40                  45
```

```
Pro Glu Thr Ile Thr Glu Ile Arg Leu Glu Gln Asn Ser Ile Arg Val
    50                  55                  60

Ile Pro Pro Gly Ala Phe Ser Pro Tyr Lys Lys Leu Arg Arg Leu Asp
65                  70                  75                  80

Leu Ser Asn Asn Gln Ile Ser Glu Leu Ala Pro Asp Ala Phe Gln Gly
                85                  90                  95

Leu Arg Ser Leu Asn Ser Leu Val Leu Tyr Gly Asn Lys Ile Thr Glu
            100                 105                 110

Leu Pro Lys Ser Leu Phe Glu Gly Leu Phe Ser Leu Gln Leu Leu Leu
        115                 120                 125

Leu Asn Ala Asn Lys Ile Asn Cys Leu Arg Val Asp Ala Phe Gln Asp
    130                 135                 140

Leu His Asn Leu Asn Leu Leu Ser Leu Tyr Asp Asn Lys Leu Gln Thr
145                 150                 155                 160

Val Ala Lys Gly Thr Phe Ser Ala Leu Arg Ala Ile Gln Thr Met His
                165                 170                 175

Leu Ala Gln Asn Pro Phe Ile Cys Asp Cys His Leu Lys Trp Leu Ala
            180                 185                 190

Asp Tyr Leu His Thr Asn Pro Ile Glu Thr Ser Gly Ala Arg Cys Thr
        195                 200                 205

Ser Pro Arg Arg Leu Ala Asn Lys Arg Ile Gly Gln Ile Lys Ser Lys
    210                 215                 220

Lys Phe Arg Cys Ser Gly Ser Ala His His His His His His
225                 230                 235

<210> SEQ ID NO 19
<211> LENGTH: 726
<212> TYPE: DNA
<213> ORGANISM: Homo sapiens
<220> FEATURE:
<221> NAME/KEY: CDS
<222> LOCATION: (1)..(726)

<400> SEQUENCE: 19 atg tac agg atg caa ctc ctg tct tgc att gca cta agt ctt gca ctt    48
Met Tyr Arg Met Gln Leu Leu Ser Cys Ile Ala Leu Ser Leu Ala Leu
1               5                   10                  15 gtc acg aat tca ctg tcc tcc ggc tcc tgc ccg gcc atg tgc acc tgc    96
Val Thr Asn Ser Leu Ser Ser Gly Ser Cys Pro Ala Met Cys Thr Cys
                20                  25                  30 agc aat ggc atc gtg gac tgt cgt gga aaa ggc ctc act gcc atc ccg   144
Ser Asn Gly Ile Val Asp Cys Arg Gly Lys Gly Leu Thr Ala Ile Pro
            35                  40                  45 gcc aac ctg ccc gag acc atg acg gag ata cgc ctg gag ctg aac ggc   192
Ala Asn Leu Pro Glu Thr Met Thr Glu Ile Arg Leu Glu Leu Asn Gly
        50                  55                  60 atc aag tcc atc cct cct gga gcc ttc tca ccc tac aga aag cta cgg   240
Ile Lys Ser Ile Pro Pro Gly Ala Phe Ser Pro Tyr Arg Lys Leu Arg
65                  70                  75                  80 agg ata gac ctg agc aac aat cag atc gct gag att gca ccc gac gcc   288
Arg Ile Asp Leu Ser Asn Asn Gln Ile Ala Glu Ile Ala Pro Asp Ala
                85                  90                  95 ttc cag ggc ctc cgc tcc ctg aac tcg ctg gtc ctc tat gga aac aag   336
Phe Gln Gly Leu Arg Ser Leu Asn Ser Leu Val Leu Tyr Gly Asn Lys
            100                 105                 110 atc aca gac ctc ccc cgt ggt gtg ttt gga ggc cta tac acc cta cag   384
Ile Thr Asp Leu Pro Arg Gly Val Phe Gly Gly Leu Tyr Thr Leu Gln
        115                 120                 125
```

```
ctc ctg ctc ctg aat gcc aac aag atc aac tgc atc cgg ccc gat gcc      432
Leu Leu Leu Leu Asn Ala Asn Lys Ile Asn Cys Ile Arg Pro Asp Ala
130                 135                 140 ttc cag gac ctg cag aac ctc tca ctg ctc tcc ctg tat gac aac aag      480
Phe Gln Asp Leu Gln Asn Leu Ser Leu Leu Ser Leu Tyr Asp Asn Lys
145                 150                 155                 160 atc cag agc ctc gcc aag ggc act ttc acc tcc ctg cgg gcc atc cag      528
Ile Gln Ser Leu Ala Lys Gly Thr Phe Thr Ser Leu Arg Ala Ile Gln
                165                 170                 175 act ctg cac ctg gcc cag aac cct ttc att tgc gac tgt aac ctc aag      576
Thr Leu His Leu Ala Gln Asn Pro Phe Ile Cys Asp Cys Asn Leu Lys
            180                 185                 190 tgg ctg gca gac ttc ctg cgc acc aat ccc atc gag acg agt ggt gcc      624
Trp Leu Ala Asp Phe Leu Arg Thr Asn Pro Ile Glu Thr Ser Gly Ala
        195                 200                 205 cgc tgt gcc agt ccc cgg cgc ctc gcc aac aag cgc atc ggg cag atc      672
Arg Cys Ala Ser Pro Arg Arg Leu Ala Asn Lys Arg Ile Gly Gln Ile
    210                 215                 220 aag agc aag aag ttc cgg tgc tca ggt agc gct cat cac cat cat cat      720
Lys Ser Lys Lys Phe Arg Cys Ser Gly Ser Ala His His His His His
225                 230                 235                 240 cac tga                                                              726
His
```

```
<210> SEQ ID NO 20
<211> LENGTH: 241
<212> TYPE: PRT
<213> ORGANISM: Homo sapiens

<400> SEQUENCE: 20

Met Tyr Arg Met Gln Leu Leu Ser Cys Ile Ala Leu Ser Leu Ala Leu
1               5                   10                  15

Val Thr Asn Ser Leu Ser Ser Gly Ser Cys Pro Ala Met Cys Thr Cys
                20                  25                  30

Ser Asn Gly Ile Val Asp Cys Arg Gly Lys Gly Leu Thr Ala Ile Pro
            35                  40                  45

Ala Asn Leu Pro Glu Thr Met Thr Glu Ile Arg Leu Glu Leu Asn Gly
        50                  55                  60

Ile Lys Ser Ile Pro Pro Gly Ala Phe Ser Pro Tyr Arg Lys Leu Arg
65                  70                  75                  80

Arg Ile Asp Leu Ser Asn Asn Gln Ile Ala Glu Ile Ala Pro Asp Ala
                85                  90                  95

Phe Gln Gly Leu Arg Ser Leu Asn Ser Leu Val Leu Tyr Gly Asn Lys
            100                 105                 110

Ile Thr Asp Leu Pro Arg Gly Val Phe Gly Gly Leu Tyr Thr Leu Gln
        115                 120                 125

Leu Leu Leu Leu Asn Ala Asn Lys Ile Asn Cys Ile Arg Pro Asp Ala
130                 135                 140

Phe Gln Asp Leu Gln Asn Leu Ser Leu Leu Ser Leu Tyr Asp Asn Lys
145                 150                 155                 160

Ile Gln Ser Leu Ala Lys Gly Thr Phe Thr Ser Leu Arg Ala Ile Gln
                165                 170                 175

Thr Leu His Leu Ala Gln Asn Pro Phe Ile Cys Asp Cys Asn Leu Lys
            180                 185                 190

Trp Leu Ala Asp Phe Leu Arg Thr Asn Pro Ile Glu Thr Ser Gly Ala
        195                 200                 205
```

```
Arg Cys Ala Ser Pro Arg Arg Leu Ala Asn Lys Arg Ile Gly Gln Ile
    210                 215                 220

Lys Ser Lys Lys Phe Arg Cys Ser Gly Ser Ala His His His His His
225                 230                 235                 240

His
```

<210> SEQ ID NO 21
<211> LENGTH: 726
<212> TYPE: DNA
<213> ORGANISM: Homo sapiens
<220> FEATURE:
<221> NAME/KEY: CDS
<222> LOCATION: (1)..(726)

<400> SEQUENCE: 21

```
atg tac agg atg caa ctc ctg tct tgc att gca cta agt ctt gca ctt      48
Met Tyr Arg Met Gln Leu Leu Ser Cys Ile Ala Leu Ser Leu Ala Leu
1               5                   10                  15 gtc acg aat tca gcc aac tcc atc tcc tgc cct tcg ccc tgc acg tgc      96
Val Thr Asn Ser Ala Asn Ser Ile Ser Cys Pro Ser Pro Cys Thr Cys
                20                  25                  30 agc aat aac atc gtg gac tgt cga gga aag ggc ttg atg gag att cct     144
Ser Asn Asn Ile Val Asp Cys Arg Gly Lys Gly Leu Met Glu Ile Pro
            35                  40                  45 gcc aac ttg ccg gag ggc atc gtc gaa ata cgc cta gaa cag aac tcc     192
Ala Asn Leu Pro Glu Gly Ile Val Glu Ile Arg Leu Glu Gln Asn Ser
    50                  55                  60 atc aaa gcc atc cct gca gga gcc ttc acc cag tac aag aaa ctg aag     240
Ile Lys Ala Ile Pro Ala Gly Ala Phe Thr Gln Tyr Lys Lys Leu Lys
65                  70                  75                  80 cga ata gac atc agc aag aat cag ata tcg gat att gct cca gat gcc     288
Arg Ile Asp Ile Ser Lys Asn Gln Ile Ser Asp Ile Ala Pro Asp Ala
                85                  90                  95 ttc cag ggc ctg aaa tca ctc aca tcg ctg gtc ctg tat ggg aac aag     336
Phe Gln Gly Leu Lys Ser Leu Thr Ser Leu Val Leu Tyr Gly Asn Lys
            100                 105                 110 atc acc gag att gcc aag gga ctg ttt gat ggg ctg gtg tcc cta cag     384
Ile Thr Glu Ile Ala Lys Gly Leu Phe Asp Gly Leu Val Ser Leu Gln
        115                 120                 125 ctg ctc ctc ctc aat gcc aac aag atc aac tgc ctg cgg gtg aac acg     432
Leu Leu Leu Leu Asn Ala Asn Lys Ile Asn Cys Leu Arg Val Asn Thr
    130                 135                 140 ttt cag gac ctg cag aac ctc aac ttg ctc tcc ctg tat gac aac aag     480
Phe Gln Asp Leu Gln Asn Leu Asn Leu Leu Ser Leu Tyr Asp Asn Lys
145                 150                 155                 160 ctg cag acc atc agc aag ggg ctc ttc gcc cct ctg cag tcc atc cag     528
Leu Gln Thr Ile Ser Lys Gly Leu Phe Ala Pro Leu Gln Ser Ile Gln
                165                 170                 175 aca ctc cac tta gcc caa aac cca ttt gtg tgc gac tgc cac ttg aag     576
Thr Leu His Leu Ala Gln Asn Pro Phe Val Cys Asp Cys His Leu Lys
            180                 185                 190 tgg ctg gcc gac tac ctc cag gac aac ccc atc gag aca agc ggg gcc     624
Trp Leu Ala Asp Tyr Leu Gln Asp Asn Pro Ile Glu Thr Ser Gly Ala
        195                 200                 205 cgc tgc agc agc ccg cgc gga ctc gcc aac aag cgc atc agc cag atc     672
Arg Cys Ser Ser Pro Arg Arg Leu Ala Asn Lys Arg Ile Ser Gln Ile
    210                 215                 220 aag agc aag aag ttc cgg tgc tca ggt agc gct cat cac cat cat cat     720
Lys Ser Lys Lys Phe Arg Cys Ser Gly Ser Ala His His His His His
225                 230                 235                 240
``` cac tga    726
His

<210> SEQ ID NO 22
<211> LENGTH: 241
<212> TYPE: PRT
<213> ORGANISM: Homo sapiens

<400> SEQUENCE: 22

Met Tyr Arg Met Gln Leu Leu Ser Cys Ile Ala Leu Ser Leu Ala Leu
1               5                   10                  15

Val Thr Asn Ser Ala Asn Ser Ile Ser Cys Pro Ser Pro Cys Thr Cys
                20                  25                  30

Ser Asn Asn Ile Val Asp Cys Arg Gly Lys Gly Leu Met Glu Ile Pro
            35                  40                  45

Ala Asn Leu Pro Glu Gly Ile Val Glu Ile Arg Leu Glu Gln Asn Ser
        50                  55                  60

Ile Lys Ala Ile Pro Ala Gly Ala Phe Thr Gln Tyr Lys Lys Leu Lys
65                  70                  75                  80

Arg Ile Asp Ile Ser Lys Asn Gln Ile Ser Asp Ile Ala Pro Asp Ala
                85                  90                  95

Phe Gln Gly Leu Lys Ser Leu Thr Ser Leu Val Leu Tyr Gly Asn Lys
            100                 105                 110

Ile Thr Glu Ile Ala Lys Gly Leu Phe Asp Gly Leu Val Ser Leu Gln
        115                 120                 125

Leu Leu Leu Leu Asn Ala Asn Lys Ile Asn Cys Leu Arg Val Asn Thr
    130                 135                 140

Phe Gln Asp Leu Gln Asn Leu Asn Leu Leu Ser Leu Tyr Asp Asn Lys
145                 150                 155                 160

Leu Gln Thr Ile Ser Lys Gly Leu Phe Ala Pro Leu Gln Ser Ile Gln
                165                 170                 175

Thr Leu His Leu Ala Gln Asn Pro Phe Val Cys Asp Cys His Leu Lys
            180                 185                 190

Trp Leu Ala Asp Tyr Leu Gln Asp Asn Pro Ile Glu Thr Ser Gly Ala
        195                 200                 205

Arg Cys Ser Ser Pro Arg Arg Leu Ala Asn Lys Arg Ile Ser Gln Ile
    210                 215                 220

Lys Ser Lys Lys Phe Arg Cys Ser Gly Ser Ala His His His His His
225                 230                 235                 240

His

<210> SEQ ID NO 23
<211> LENGTH: 1362
<212> TYPE: DNA
<213> ORGANISM: Homo sapiens
<220> FEATURE:
<221> NAME/KEY: CDS
<222> LOCATION: (1)..(1362)

<400> SEQUENCE: 23 atg tac agg atg caa ctc ctg tct tgc att gca cta agt ctt gca ctt    48
Met Tyr Arg Met Gln Leu Leu Ser Cys Ile Ala Leu Ser Leu Ala Leu
1               5                   10                  15 gtc acg aat tca ctt cgt cag gaa gat ttt cca cct cgc att gtt gaa    96
Val Thr Asn Ser Leu Arg Gln Glu Asp Phe Pro Pro Arg Ile Val Glu
                20                  25                  30 cac cct tca gac ctg att gtc tca aaa gga gaa cct gca act ttg aac   144
His Pro Ser Asp Leu Ile Val Ser Lys Gly Glu Pro Ala Thr Leu Asn -continued

|  |  |  |  |  | 35 |  |  |  | 40 |  |  |  |  | 45 |  |  |  |
|---|---|---|---|---|---|---|---|---|---|---|---|---|---|---|---|---|---|
| tgc | aaa | gct | gaa | ggc | cgc | ccc | aca | ccc | act | att | gaa | tgg | tac | aaa | ggg |  | 192 |
| Cys | Lys | Ala | Glu | Gly | Arg | Pro | Thr | Pro | Thr | Ile | Glu | Trp | Tyr | Lys | Gly |  |  |
|  |  |  | 50 |  |  |  | 55 |  |  |  |  | 60 |  |  |  |  |  |
| gga | gag | aga | gtg | gag | aca | gac | aaa | gat | gac | cct | cgc | tca | cac | cga | atg |  | 240 |
| Gly | Glu | Arg | Val | Glu | Thr | Asp | Lys | Asp | Asp | Pro | Arg | Ser | His | Arg | Met |  |  |
| 65 |  |  |  |  | 70 |  |  |  |  | 75 |  |  |  |  | 80 |  |  |
| ttg | ctg | ccg | agt | gga | tct | tta | ttt | ttc | tta | cgt | ata | gta | cat | gga | cgg |  | 288 |
| Leu | Leu | Pro | Ser | Gly | Ser | Leu | Phe | Phe | Leu | Arg | Ile | Val | His | Gly | Arg |  |  |
|  |  |  |  | 85 |  |  |  |  | 90 |  |  |  |  | 95 |  |  |  |
| aaa | agt | aga | cct | gat | gaa | gga | gtc | tat | gtc | tgt | gta | gca | agg | aat | tac |  | 336 |
| Lys | Ser | Arg | Pro | Asp | Glu | Gly | Val | Tyr | Val | Cys | Val | Ala | Arg | Asn | Tyr |  |  |
|  |  |  | 100 |  |  |  |  | 105 |  |  |  |  | 110 |  |  |  |  |
| ctt | gga | gag | gct | gtg | agc | cac | aat | gca | tcg | ctg | gaa | gta | gcc | ata | ctt |  | 384 |
| Leu | Gly | Glu | Ala | Val | Ser | His | Asn | Ala | Ser | Leu | Glu | Val | Ala | Ile | Leu |  |  |
|  |  | 115 |  |  |  |  | 120 |  |  |  |  | 125 |  |  |  |  |  |
| cgg | gat | gac | ttc | aga | caa | aac | cct | tcg | gat | gtc | atg | gtt | gca | gta | gga |  | 432 |
| Arg | Asp | Asp | Phe | Arg | Gln | Asn | Pro | Ser | Asp | Val | Met | Val | Ala | Val | Gly |  |  |
|  | 130 |  |  |  |  | 135 |  |  |  |  | 140 |  |  |  |  |  |  |
| gag | cct | gca | gta | atg | gaa | tgc | caa | cct | cca | cga | ggc | cat | cct | gag | ccc |  | 480 |
| Glu | Pro | Ala | Val | Met | Glu | Cys | Gln | Pro | Pro | Arg | Gly | His | Pro | Glu | Pro |  |  |
| 145 |  |  |  |  | 150 |  |  |  |  | 155 |  |  |  |  | 160 |  |  |
| acc | att | tca | tgg | aag | aaa | gat | ggc | tct | cca | ctg | gat | gat | aaa | gat | gaa |  | 528 |
| Thr | Ile | Ser | Trp | Lys | Lys | Asp | Gly | Ser | Pro | Leu | Asp | Asp | Lys | Asp | Glu |  |  |
|  |  |  |  | 165 |  |  |  |  | 170 |  |  |  |  | 175 |  |  |  |
| aga | ata | act | ata | cga | gga | gga | aag | ctc | atg | atc | act | tac | acc | cgt | aaa |  | 576 |
| Arg | Ile | Thr | Ile | Arg | Gly | Gly | Lys | Leu | Met | Ile | Thr | Tyr | Thr | Arg | Lys |  |  |
|  |  |  | 180 |  |  |  |  | 185 |  |  |  |  | 190 |  |  |  |  |
| agt | gac | gct | ggc | aaa | tat | gtt | tgt | gtt | ggt | acc | aat | atg | gtt | ggg | gaa |  | 624 |
| Ser | Asp | Ala | Gly | Lys | Tyr | Val | Cys | Val | Gly | Thr | Asn | Met | Val | Gly | Glu |  |  |
|  |  | 195 |  |  |  |  | 200 |  |  |  |  | 205 |  |  |  |  |  |
| cgt | gag | agt | gaa | gta | gcc | gag | ctg | act | gtc | tta | gag | aga | cca | tca | ttt |  | 672 |
| Arg | Glu | Ser | Glu | Val | Ala | Glu | Leu | Thr | Val | Leu | Glu | Arg | Pro | Ser | Phe |  |  |
|  | 210 |  |  |  |  | 215 |  |  |  |  | 220 |  |  |  |  |  |  |
| gtg | gag | tcc | aag | tac | ggc | cct | cct | tgc | cct | ccc | tgc | cct | gcc | cct | gag |  | 720 |
| Val | Glu | Ser | Lys | Tyr | Gly | Pro | Pro | Cys | Pro | Pro | Cys | Pro | Ala | Pro | Glu |  |  |
| 225 |  |  |  |  | 230 |  |  |  |  | 235 |  |  |  |  | 240 |  |  |
| ttc | gag | ggc | gga | cct | agc | gtg | ttc | ctg | ttc | cct | cct | aag | cct | aag | gac |  | 768 |
| Phe | Glu | Gly | Gly | Pro | Ser | Val | Phe | Leu | Phe | Pro | Pro | Lys | Pro | Lys | Asp |  |  |
|  |  |  |  | 245 |  |  |  |  | 250 |  |  |  |  | 255 |  |  |  |
| acc | ctg | atg | atc | tcc | cgg | acc | cct | gag | gtg | acc | tgt | gtg | gtg | gtg | gac |  | 816 |
| Thr | Leu | Met | Ile | Ser | Arg | Thr | Pro | Glu | Val | Thr | Cys | Val | Val | Val | Asp |  |  |
|  |  |  | 260 |  |  |  |  | 265 |  |  |  |  | 270 |  |  |  |  |
| gtg | tcc | cag | gag | gac | cct | gag | gtc | cag | ttc | aac | tgg | tac | gtg | gac | ggc |  | 864 |
| Val | Ser | Gln | Glu | Asp | Pro | Glu | Val | Gln | Phe | Asn | Trp | Tyr | Val | Asp | Gly |  |  |
|  |  | 275 |  |  |  |  | 280 |  |  |  |  | 285 |  |  |  |  |  |
| gtg | gag | gtg | cac | aac | gcc | aag | acc | aag | cct | cgg | gag | gag | cag | ttc | aat |  | 912 |
| Val | Glu | Val | His | Asn | Ala | Lys | Thr | Lys | Pro | Arg | Glu | Glu | Gln | Phe | Asn |  |  |
|  | 290 |  |  |  |  | 295 |  |  |  |  | 300 |  |  |  |  |  |  |
| tcc | acc | tac | cgg | gtg | gtg | tct | gtg | ctg | acc | gtg | ctg | cac | cag | gac | tgg |  | 960 |
| Ser | Thr | Tyr | Arg | Val | Val | Ser | Val | Leu | Thr | Val | Leu | His | Gln | Asp | Trp |  |  |
| 305 |  |  |  |  | 310 |  |  |  |  | 315 |  |  |  |  | 320 |  |  |
| ctg | aac | ggc | aaa | gaa | tac | aag | tgt | aag | gtc | tcc | aac | aag | ggc | ctg | ccc |  | 1008 |
| Leu | Asn | Gly | Lys | Glu | Tyr | Lys | Cys | Lys | Val | Ser | Asn | Lys | Gly | Leu | Pro |  |  |
|  |  |  |  | 325 |  |  |  |  | 330 |  |  |  |  | 335 |  |  |  |
| tcc | tcc | atc | gag | aaa | acc | atc | tcc | aag | gcc | aag | ggc | cag | cct | agg | gag |  | 1056 |
| Ser | Ser | Ile | Glu | Lys | Thr | Ile | Ser | Lys | Ala | Lys | Gly | Gln | Pro | Arg | Glu |  |  |
|  |  |  | 340 |  |  |  |  | 345 |  |  |  |  | 350 |  |  |  |  |
| cct | cag | gtg | tac | acc | ctg | cct | cct | agc | cag | gaa | gag | atg | acc | aag | aac |  | 1104 |

```
                Pro Gln Val Tyr Thr Leu Pro Pro Ser Gln Glu Glu Met Thr Lys Asn
                                355                 360                 365 cag gtg tcc ctg acc tgt ctg gtg aag ggc ttc tac cct tcc gac atc          1152
Gln Val Ser Leu Thr Cys Leu Val Lys Gly Phe Tyr Pro Ser Asp Ile
        370                 375                 380 gcc gtg gag tgg gag tcc aac ggc cag cct gag aac aac tac aag acc          1200
Ala Val Glu Trp Glu Ser Asn Gly Gln Pro Glu Asn Asn Tyr Lys Thr
385                 390                 395                 400 acc cct cct gtg ctg gac tcc gac ggc tcc ttc ttc ctg tac tcc agg          1248
Thr Pro Pro Val Leu Asp Ser Asp Gly Ser Phe Phe Leu Tyr Ser Arg
                405                 410                 415 ctg acc gtg gac aag tcc cgg tgg cag gag ggc aac gtc ttt tcc tgc          1296
Leu Thr Val Asp Lys Ser Arg Trp Gln Glu Gly Asn Val Phe Ser Cys
        420                 425                 430 tcc gtg atg cac gag gcc ctg cac aac cac tac acc cag aag tcc ctg          1344
Ser Val Met His Glu Ala Leu His Asn His Tyr Thr Gln Lys Ser Leu
435                 440                 445 tcc ctg tct ctg ggc tga                                                  1362
Ser Leu Ser Leu Gly
        450

<210> SEQ ID NO 24
<211> LENGTH: 453
<212> TYPE: PRT
<213> ORGANISM: Homo sapiens

<400> SEQUENCE: 24

Met Tyr Arg Met Gln Leu Leu Ser Cys Ile Ala Leu Ser Leu Ala Leu
1               5                   10                  15

Val Thr Asn Ser Leu Arg Gln Glu Asp Phe Pro Arg Ile Val Glu
            20                  25                  30

His Pro Ser Asp Leu Ile Val Ser Lys Gly Glu Pro Ala Thr Leu Asn
        35                  40                  45

Cys Lys Ala Glu Gly Arg Pro Thr Pro Thr Ile Glu Trp Tyr Lys Gly
    50                  55                  60

Gly Glu Arg Val Glu Thr Asp Lys Asp Asp Pro Arg Ser His Arg Met
65                  70                  75                  80

Leu Leu Pro Ser Gly Ser Leu Phe Phe Leu Arg Ile Val His Gly Arg
                85                  90                  95

Lys Ser Arg Pro Asp Glu Gly Val Tyr Val Cys Val Ala Arg Asn Tyr
            100                 105                 110

Leu Gly Glu Ala Val Ser His Asn Ala Ser Leu Glu Val Ala Ile Leu
        115                 120                 125

Arg Asp Asp Phe Arg Gln Asn Pro Ser Asp Val Met Val Ala Val Gly
    130                 135                 140

Glu Pro Ala Val Met Glu Cys Gln Pro Pro Arg Gly His Pro Glu Pro
145                 150                 155                 160

Thr Ile Ser Trp Lys Lys Asp Gly Ser Pro Leu Asp Asp Lys Asp Glu
                165                 170                 175

Arg Ile Thr Ile Arg Gly Gly Lys Leu Met Ile Thr Tyr Thr Arg Lys
            180                 185                 190

Ser Asp Ala Gly Lys Tyr Val Cys Val Gly Thr Asn Met Val Gly Glu
        195                 200                 205

Arg Glu Ser Glu Val Ala Glu Leu Thr Val Leu Glu Arg Pro Ser Phe
    210                 215                 220

Val Glu Ser Lys Tyr Gly Pro Pro Cys Pro Pro Cys Pro Ala Pro Glu
225                 230                 235                 240
```

```
Phe Glu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
            435                 440                 445

Ser Leu Ser Leu Gly
    450
```